(12) United States Patent
Gaunt et al.

(10) Patent No.: US 9,648,884 B2
(45) Date of Patent: May 16, 2017

(54) SODIUM BICARBONATE PRODUCT

(71) Applicant: Eminate Limited, Nottinghamshire (GB)

(72) Inventors: Sarah Gaunt, Nottinghamshire (GB); Stephen John Minter, Derbyshire (GB); Edna Elaine Best, Nottingham (GB); Warren L. Nehmer, Decatur, IL (US)

(73) Assignee: Eminate Limited, Nottingham, Nottinghamshire (GB)

( * ) Notice: Subject to any disclaimer, the term of this patent is extended or adjusted under 35 U.S.C. 154(b) by 0 days.

(21) Appl. No.: 14/380,027

(22) PCT Filed: Feb. 20, 2013

(86) PCT No.: PCT/GB2013/050412
§ 371 (c)(1),
(2) Date: Aug. 20, 2014

(87) PCT Pub. No.: WO2013/124652
PCT Pub. Date: Aug. 29, 2013

(65) Prior Publication Data
US 2015/0071979 A1 Mar. 12, 2015

(30) Foreign Application Priority Data
Feb. 20, 2012 (GB) .................................. 1202797.5

(51) Int. Cl.
| | |
|---|---|
| C01D 7/06 | (2006.01) |
| C01D 7/24 | (2006.01) |
| A21D 10/00 | (2006.01) |
| C01D 7/00 | (2006.01) |
| C01D 7/38 | (2006.01) |
| A21D 2/02 | (2006.01) |
| A21D 2/18 | (2006.01) |
| A01N 25/12 | (2006.01) |
| A01N 59/00 | (2006.01) |
| A21D 2/14 | (2006.01) |
| C08K 3/26 | (2006.01) |
| C08L 3/00 | (2006.01) |
| C08L 5/00 | (2006.01) |
| C08L 5/06 | (2006.01) |
| C08L 5/12 | (2006.01) |
| A23L 33/16 | (2016.01) |

(52) U.S. Cl.
CPC ........... *A21D 10/005* (2013.01); *A01N 25/12* (2013.01); *A01N 59/00* (2013.01); *A21D 2/02* (2013.01); *A21D 2/14* (2013.01); *A21D 2/18* (2013.01); *A21D 2/181* (2013.01); *A21D 2/183* (2013.01); *A23L 33/16* (2016.08); *C01D 7/00* (2013.01); *C01D 7/38* (2013.01); *C08K 3/26* (2013.01); *C08L 3/00* (2013.01); *C08L 5/00* (2013.01); *C08L 5/06* (2013.01); *C08L 5/12* (2013.01); *C08K 2003/262* (2013.01); *Y10T 428/2982* (2015.01)

(58) Field of Classification Search
CPC .............. A23L 1/304; C01D 7/24; C01D 9/00
See application file for complete search history.

(56) References Cited

U.S. PATENT DOCUMENTS

| | | | |
|---|---|---|---|
| 3,647,365 A | 3/1972 | Saeman | |
| 4,900,577 A * | 2/1990 | Arciszewski ............ | A21D 2/02 426/562 |
| 5,262,134 A * | 11/1993 | Frint ........................ | C01D 7/14 23/302 T |
| 5,417,963 A * | 5/1995 | Murphy et al. .................. | 424/65 |
| 5,482,702 A | 1/1996 | Murphy et al. | |
| 5,693,334 A | 12/1997 | Miskewitz | |
| 8,470,055 B2 * | 6/2013 | Cui .......................... | C01D 7/24 23/302 T |
| 2011/0112207 A1* | 5/2011 | Tinson ..................... | C01D 7/02 521/88 |

FOREIGN PATENT DOCUMENTS

| | | |
|---|---|---|
| JP | H05076309 A | 3/1993 |
| JP | 2001270956 A | 10/2001 |
| JP | 2005200282 A | 7/2005 |
| WO | 2009/133409 | 11/2009 |

OTHER PUBLICATIONS

Corral et al., "Antimicrobial activity of sodium bicarbonate", J of Food Sci., vol. 53, No. 3, 1988, p. 981-2.*
International Preliminary Report on Patentability mailed Sep. 4, 2014 for International Application No. PCT/GB2013/050412 filed Feb. 20, 2013.

* cited by examiner

*Primary Examiner* — Gina Justice
(74) *Attorney, Agent, or Firm* — McDonnell Boehnen Hulbert & Berghoff LLP

(57) ABSTRACT

A sodium bicarbonate product comprises particles containing sodium bicarbonate and an organic material that is a solid at ambient temperature. The particles have a structure comprised of individual crystallites of sodium bicarbonate attached together in the particle. More than 95% by volume of the particles have a size less than 200 μm. Particles of the product are hollow and are formed of an outer shell of the crystallites. The product may be used, for example, as a leavening agent in the production of cooked foods. The product may be produced by spray drying a solution or slurry dissolved organic material and dissolved sodium bicarbonate. The sodium bicarbonate may be present as a suspension.

48 Claims, 23 Drawing Sheets

Miramist SE (Modified Starch)
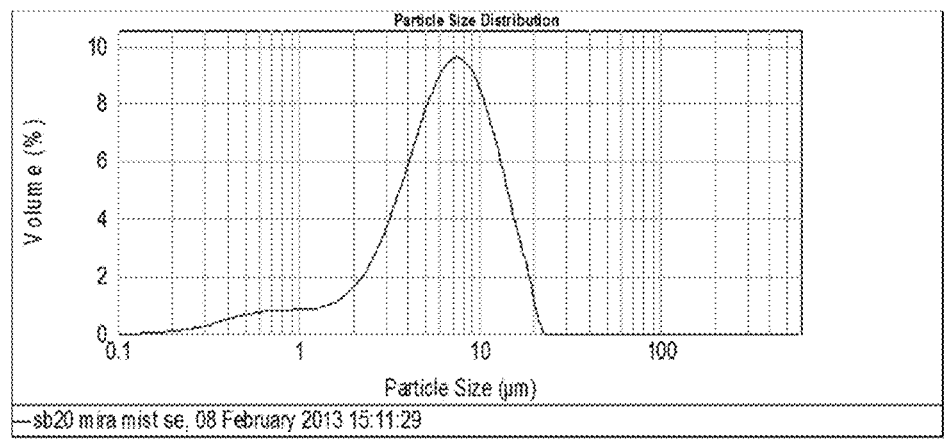
D(0.1) = 1.9 um    D(0.5) = 6.4 um    D(0.9) = 13.18 um
Fig. 15
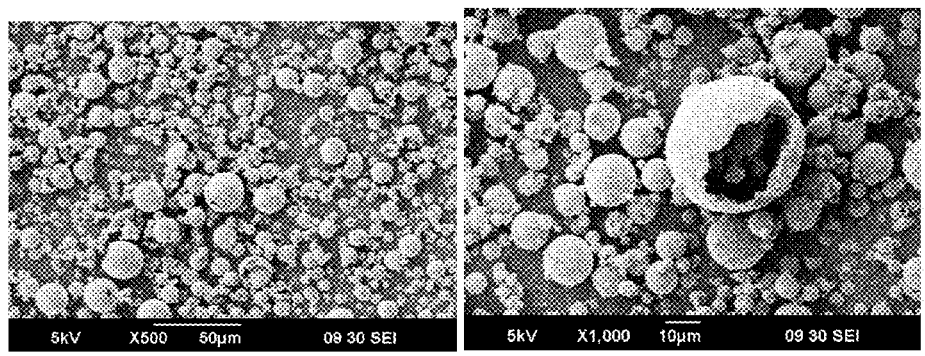
Fig. 16 (a)              Fig. 16 (b)

Promitor L70 (Soluble gluco fibre)
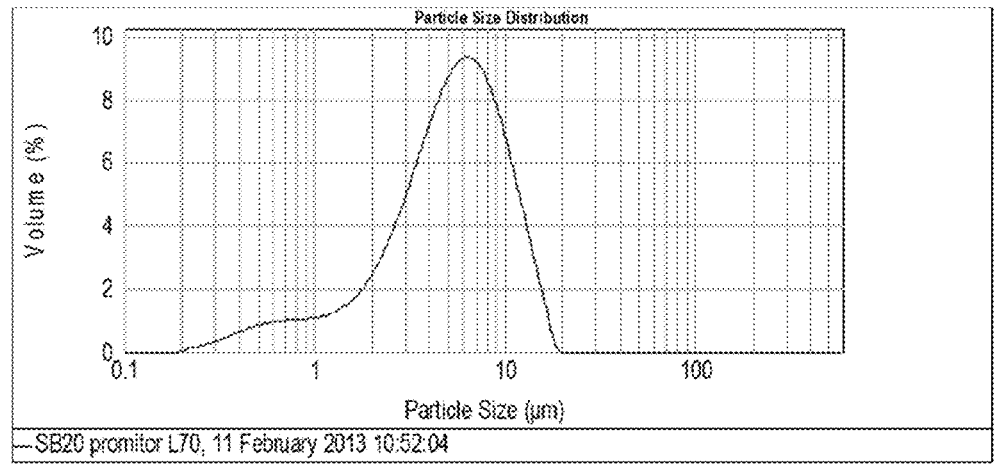
D(0.1) = 1.5 um    D(0.5) = 5.3 um    D(0.9) = 11.0 um
Fig. 17
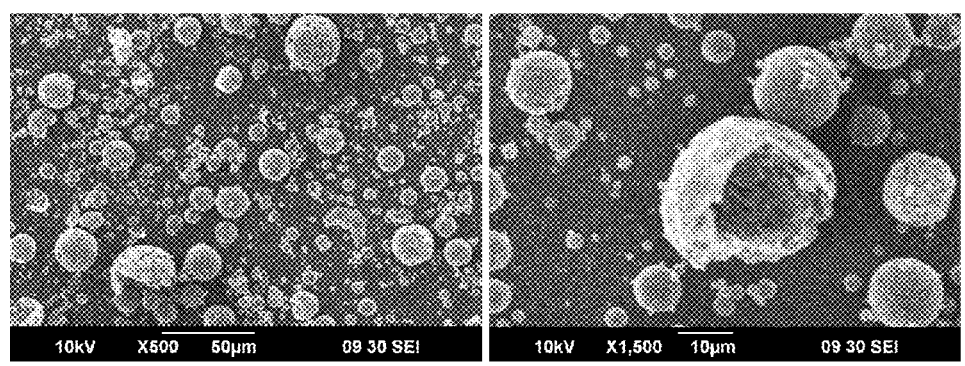
Fig. 18 (a)        Fig. 18 (b)

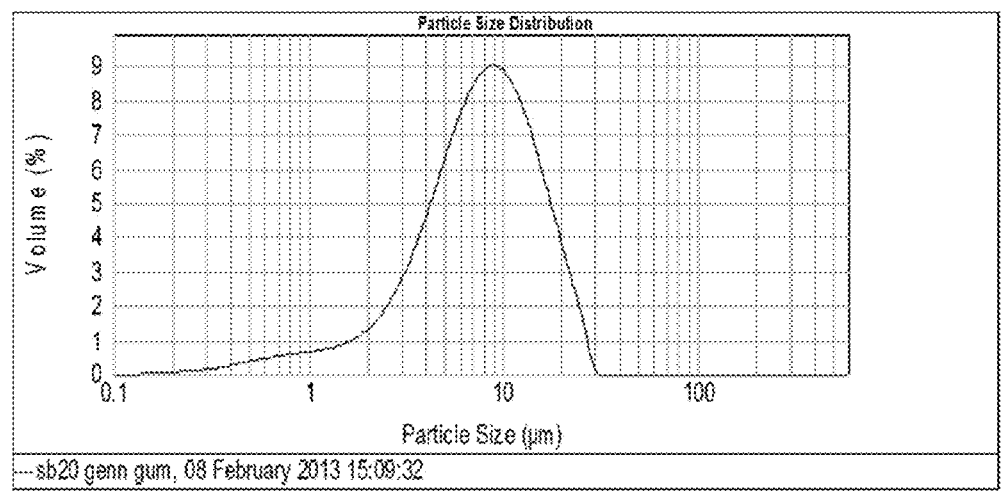
D(0.1) = 2.5 um    D(0.5) = 7.9 um    D(0.9) = 17.1 um
Fig. 19
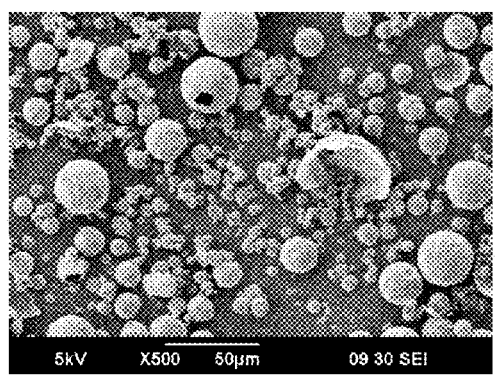 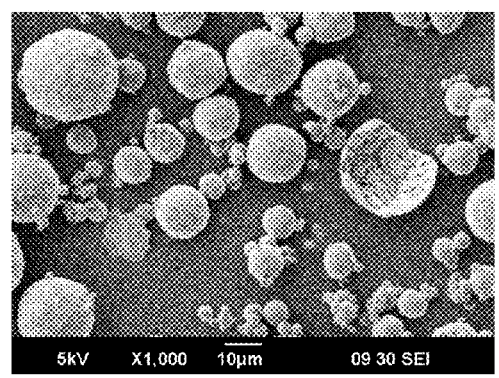
Fig. 20 (a)          Fig. 20 (b)

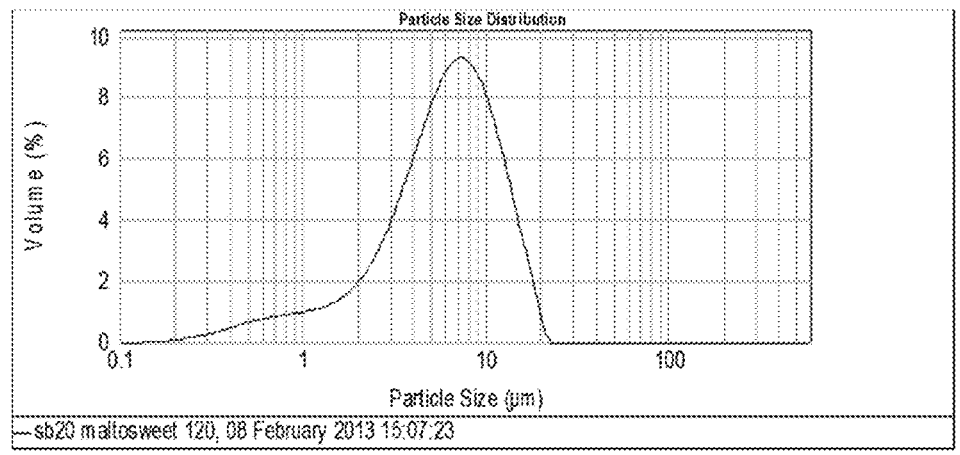
Fig. 21
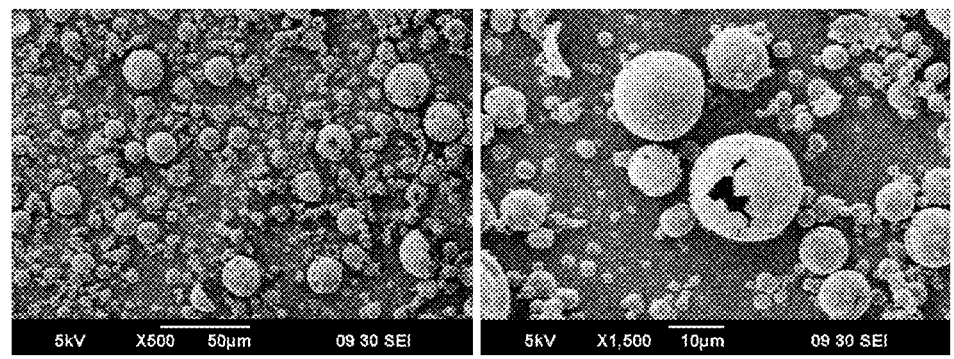
Fig. 22 (a)     Fig. 22 (b)

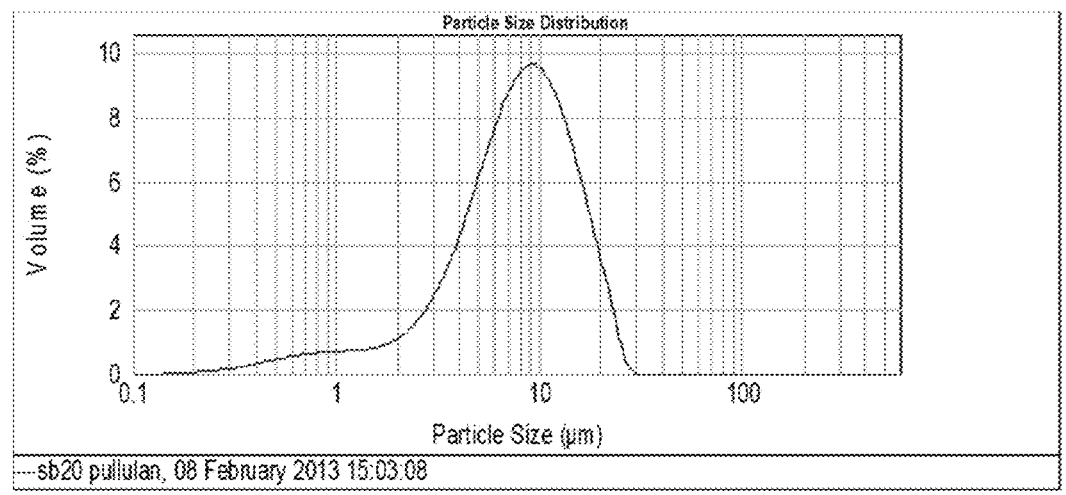
D(0.1) = 2.6 um    D(0.5) = 8.0 um    D(0.9) = 16.4 um
Fig. 25
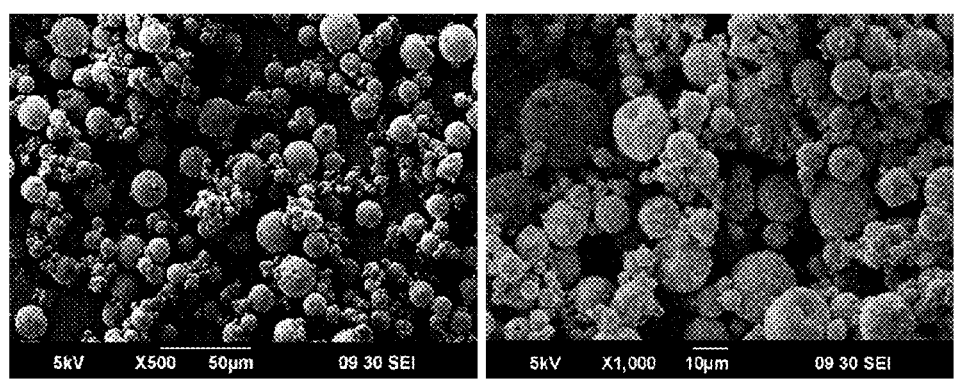
Fig. 26 (a)   Fig. 26 (b)

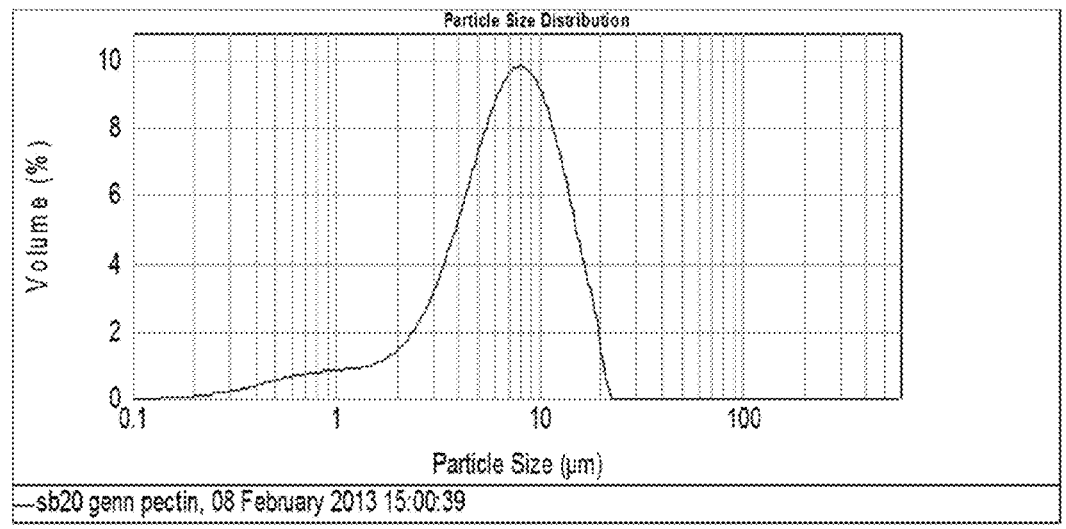
D(0.1) = 2.1 um   D(0.5) = 6.9 um   D(0.9) = 13.9 um
Fig. 27
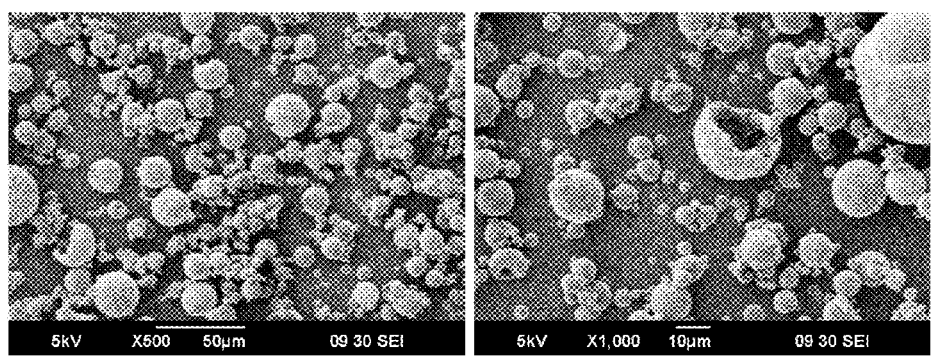
Fig. 28 (a)          Fig. 28 (b)

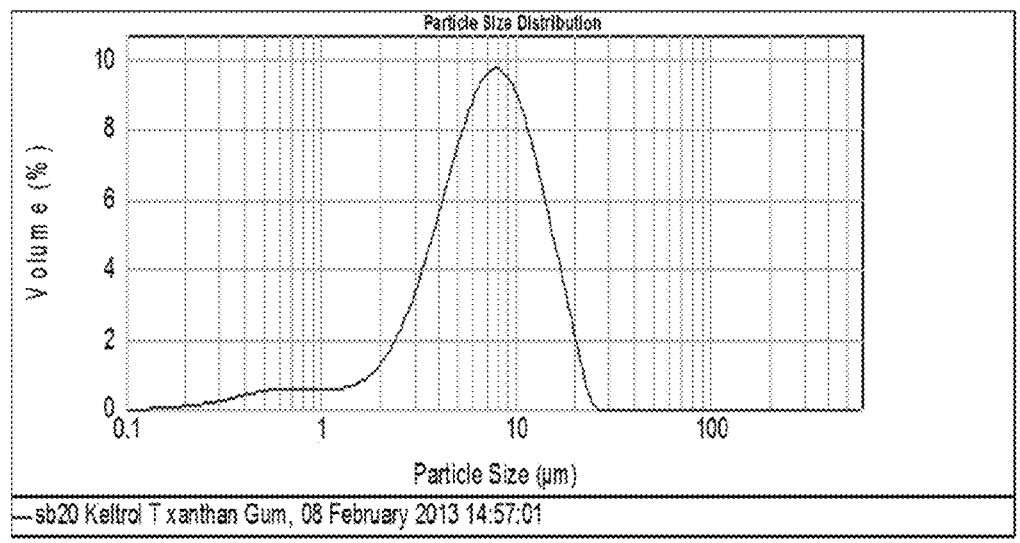
D(0.1) = 2.5 um   D(0.5) = 7.0 um   D(0.9) = 14.4 um
Fig. 29
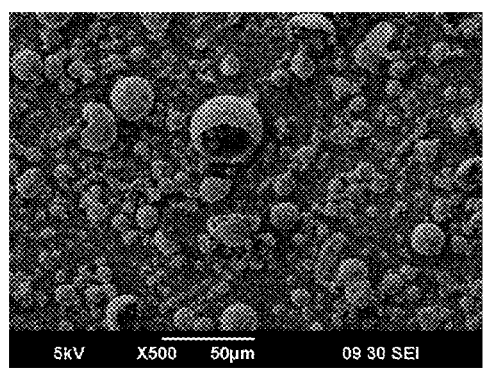
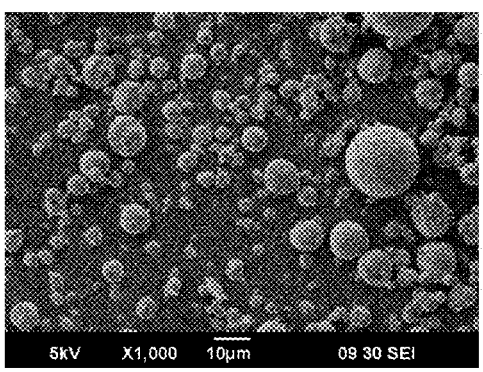
Fig. 30(a)       Fig. 30 (b)

SODIUM BICARBONATE PRODUCT

The present invention relates to sodium bicarbonate and more particularly to the preparation of a sodium bicarbonate product that is eminently suitable for use in applications where generation of carbon dioxide is required as well as in other applications. The sodium bicarbonate is eminently suitable for use as a raising (leavening) agent in the preparation of cooked food products, e.g. fried, grilled and baked products (e.g. battered foodstuffs, cakes, biscuits etc.) and also eminently suitable for uses outside the field of food where carbon dioxide generation is required, such as a foaming (blowing) agent for plastics and rubber. The sodium bicarbonate also has application for use in cleaning, industrial and household chemicals and in deodorisation and neutralisation. Further uses are in antimicrobial applications.

Sodium bicarbonate (also known as sodium hydrogen carbonate and baking soda) and has the chemical formula $NaHCO_3$. Sodium bicarbonate has applications in several areas, primarily including; cooking, health and fitness, cleaning and as a bio-control for pests. In healthcare, it has been used as the active ingredient in toothpaste, as an antacid to treat indigestion/heartburn and as a supplement for athletes in speed-based events. As a paste it is a very effective household cleaner. It is also an effective way of controlling fungus growth and is registered in the USA by the Environmental Protection Agency as a bio-pesticide. It is also sold as a cattle feed supplement, in particular as a buffering agent for the rumen. Other uses include clothing/book deodorants and to clean paintwork (soda-blasting).

Sodium bicarbonate is still used in Asian cuisine to tenderise meats. Baking soda may react with acids in food, including Vitamin C (L-ascorbic acid). It is also used in breadings such as for fried foods to enhance crispness.

Sodium bicarbonate is used in gold and platinum plating, the tanning industry, dyes and intermediates, detergents, for treating wool and silk, as the active ingredient in fire extinguishers, in flue gas treatments, as an explosion suppressant, in ceramics, in rubber and plastics, as a component of oil-well drilling fluids, in pest control and in the paper and pulp industries.

In particular, sodium bicarbonate has been used over many years as a raising agent in the preparation of cooked food items, the "raising" being effected as a result of carbon dioxide released from the sodium bicarbonate. This may generally be by one of two mechanisms. The first is reaction of the sodium bicarbonate with an acid either naturally present in the components from which the food is being prepared or added separately. For the purpose of this mechanism, sodium bicarbonate finds use as "baking powder" which comprises an admixture of sodium bicarbonate and an acid component such as an acid phosphate or cream of tartar. The second mechanism is by thermal decomposition of sodium bicarbonate to produce the carbon dioxide.

Although sodium bicarbonate is decomposed during preparation of the foodstuff, the sodium ions containing in the sodium bicarbonate still remain in the foodstuff. It is now recognised that excessive amounts of sodium in the diet are a contributory factor of high blood pressure which is a risk factor for stroke. There is thus a drive by government agencies concerned with the health of the population to reduce sodium intake. One significant source of sodium intake is common salt (sodium chloride) as used extensively for the seasoning of foodstuffs. A further significant source of sodium intake results from the use of sodium bicarbonate as a raising agent, particularly for persons who have a higher consumption of baked confectionery items such as cakes and biscuits.

At an elementary level, it could be considered that sodium intake can be reduced by, on the one hand, reducing the amount of common salt (sodium chloride) used in the preparation of foodstuffs and, on the other hand, reducing the amount of sodium bicarbonate used as raising agent in the preparation of foodstuffs. However this elementary approach gives rise to different issues as between reduction of the amounts of sodium chloride and sodium bicarbonate used in the preparation of foodstuffs. With regard to sodium chloride, a certain level is required for the "taste" of the foodstuff (many people do not like food prepared without common salt). In contrast, a certain minimum amount of sodium bicarbonate is required to generate sufficient carbon dioxide for adequate "raising" of the foodstuff.

WO 2009/133409 A (Eminate Ltd) discloses a salt product which is prepared by atomising a mixture comprised of sodium chloride dissolved in a solvent (preferably water) and an organic material that is solid under ambient temperature conditions (preferably also dissolved in the solvent) and evaporating the solvent from the atomised particles. The procedure may be effective, for example, by spray-drying. The organic material used in accordance with the teaching of WO 2009/133409 may, for example, be a carbohydrate such as maltodextrin or Gum Arabic.

The product obtained in accordance with WO 2009/133409 comprises, a generally spheroidal, hollow particles of very small size. Thus, for example, more than 95% of the particles may have a size less than 50 μm, with an average particle size being in the range of about 5 μm to 10 μm. The salt product may be used in lower amounts that conventional salt to provide the same taste impact. Additional advantages of the salt product as disclosed in WO 2009/133409 are that it is non-hydroscopic (so that it remains free-flowing over extended periods of time despite its small size) and the salt product is useful in the baking of bread where the use of lower amounts of salt does not have an adverse effect on the bread production process (the use of higher amounts of conventional salt is generally required for satisfactory bread production).

We have now surprisingly found that a sodium bicarbonate product with various advantageous properties, as detailed more fully below, may be prepared based on methods of the type disclosed in WO 2009/133409.

According to a first aspect of the present invention there is provided a sodium bicarbonate product which comprises particles containing sodium bicarbonate and an organic material that is a solid at ambient temperature, the particles of said product having a structure comprised of individual crystallites of sodium bicarbonate attached together in the particle wherein more than 95% by volume of the particles have a size less than 200 μm and wherein particles of the product are hollow and are formed of an outer shell of said crystallites.

Particle sizes as referred to herein in relation to the sodium bicarbonate product of the invention are expressed as "by volume" and are as determined using a Malvern Mastersizer 2000 laser diffractometer with a Scirocco 2000 dry powder accessory. The "Analysis Mode" setting on the diffractometer was "General Purpose (fine)" with the compound (whose particle size is to be measured) set at sodium bicarbonate.

In a second aspect, the present invention provides a method of producing the sodium bicarbonate product comprising the steps of:

(i) preparing an aqueous admixture which comprises sodium bicarbonate and a water soluble organic material that is a solid at ambient temperature, the sodium bicarbonate and the organic material both being at least partially dissolved in the aqueous phase, and (ii) atomising said admixture and evaporating water to produce a sodium bicarbonate product in which particles of said product have a structure comprised of individual crystallites of sodium bicarbonate attached together in the particle wherein more than 95% by volume of the particles have a size less than 200 μm and wherein particles of the product are hollow and are formed of an outer shell of said crystallites.

The sodium bicarbonate product in accordance with the first aspect of the invention has a number of advantageous and surprising properties. Tests have shown that, weight-for-weight, the sodium bicarbonate product of the invention generates significantly more carbon dioxide than conventional sodium bicarbonate. Alternatively, the same volume of carbon dioxide may be generated by the use of a lower amount of sodium bicarbonate product in accordance with the invention than conventional sodium bicarbonate. This is due to the small particle size of the sodium bicarbonate product and its hollow structure.

As a generality, therefore, the sodium bicarbonate product in accordance with the invention may be used to generate carbon dioxide for any application where such generation.

The sodium bicarbonate may be used as a raising agent in the preparation of cooked foodstuffs in amounts lower amounts than conventional sodium bicarbonate whilst still providing adequate levels of carbon dioxide for the raising function and producing products with good taste and texture characteristics. Thus less sodium (introduced from the sodium bicarbonate) is introduced into the food, which clearly provides health benefits.

A further use of the sodium bicarbonate, based on its enhanced carbon dioxide generation, is as a foaming (blowing) agent for plastics and rubber.

Other advantageous properties associated with the sodium bicarbonate product produced in accordance with the invention are enhanced antimicrobial activity (e.g. antibacterial/antifungal activity) as well as enhanced deodorisation and neutralisation activity as compared to conventional sodium bicarbonate. Once again this is believed to be attributable to the small particle size of the product produced in accordance with the invention.

Other applications for sodium bicarbonate produced in accordance with the method of the invention are any such application as detailed in the introduction to this specification.

The fact that a sodium bicarbonate product in accordance with the invention and having advantageous properties as outlined above may be obtained using a method based on that disclosed in WO 2009/133409 is surprising for a number of reasons. Firstly, the disclosure of WO 2009/133409 relates solely to the production of products based on sodium chloride, and does not contain any suggestion of applying the production methods disclosed therein to compounds that are capable of providing gas evolution. Secondly, our experimental work has shown that the procedure disclosed in WO 2009/133409 is not applicable to the production of hollow particles from the closely similar inorganic salts potassium bicarbonate, ammonium bicarbonate and sodium carbonate. Furthermore, we have been unable to produce hollow particles using potassium chloride, calcium chloride or magnesium chloride.

The sodium bicarbonate product in accordance with the invention is such that more than 95% (and ideally 100%) by volume of the particles have a size less than 200 μm. More preferably, more than 95% (and ideally 100%) by volume of the particles will have a particle size of less than 150 μm, still more preferably less than 125 μm, and even more preferably less than 100 μm (e.g. with all particles having a size in the range of 2 μm to 100 μm. For all of these size ranges (e.g. 95% by volume of the particle having a size less than 200 μm), the mean particle size is preferably in the range of 50 μm to 100 μm.

Further embodiments of the first aspect of the invention provide a sodium bicarbonate product in which more than 95% (and ideally 100%) by volume of the particles have a size less than 75 μm. for example more than 95% (and ideally 100%) by volume of the particles may have a size less than 50 μm. The product may be such that more than 75% by volume of the particles have a size less than 30 μm. The product may have a mean particle size of 10 to 20 μm and may be of narrow particle size distribution. In other embodiments the mean particle size may be in the range of 2 to 10 μm.

The sodium bicarbonate product of the invention comprises particles that are hollow. The hollow particles will constitute at least a fraction of the product and will preferably comprise at least 30% of the particles, more preferably at least 40%, and still more preferably comprise a substantial proportion of the product, i.e. more than 50%. The proportion of hollow particles is preferably at least 60%, more preferably at least 70%, and even more preferably at least 80%, and still more preferably at least 90%. In principle, the ideal is 100%, but in practice there may be 50-90% of hollow particles. Any "non-hollow" particles in the product will, of course be solid particles comprised of sodium bicarbonate and the organic material. The fraction of solid particles in the product will depend on the method of producing the sodium bicarbonate product (see below). The percentage of hollow particles may be assessed on a numerical basis by examining the product under a suitable magnification (e.g. in a scanning electromicrograph) and counting the number of hollow particles as compared to the solid particles. Generally a magnification of ×500 to ×2000 will be suitable for this purpose, although the skilled person can readily select the most appropriate value.

The hollow particles in the sodium bicarbonate product of the invention are comprised of an outer shell formed of individual crystallites of sodium bicarbonate attached together to form the shell, which itself surrounds the hollow interior cavity of the particle. The shell may be "complete" in the sense that the hollow interior cavity is fully encased by the shell. Alternatively, the shell may not be fully complete. The structure of such hollow sodium bicarbonate products is to our knowledge unique. When seen under a Scanning Electron Microscope at an appropriate magnification (e.g. ×5000) preferred embodiments of product in accordance with the invention have individual particles that are seen to be generally spheroidal (although not necessarily spherical in the truest geometric sense) and are of a hollow structure in which the shell is comprised of small generally rod shaped crystallites of sodium bicarbonate.

Typically, the sodium bicarbonate product of the invention will comprise 80% to 95% of sodium bicarbonate, based on the total weight of the bicarbonate and the organic material. The product may, for example, comprise 84% to 95% by weight of sodium bicarbonate on the same basis.

The organic material incorporated in the particle, and which maintains the coherency of hollow particles having a shell comprised of individual crystallites may be any one of a number of materials that is at least partially and ideally substantially soluble in water. The material may, for example, be a natural or synthetic polymer. If the sodium bicarbonate product is intended for food use then the material should be one which is acceptable for alimentary purposes. The material may, for example, be a carbohydrate, e.g. an oligosaccharide or a polysaccharide. Alternatively the material may be a protein. Mixtures of such polymer types can also be used. If the polymer is a carbohydrate then it may, for example, be one or more of maltodextrin (e.g. Fibresol), Gum Arabic, starch (e.g. soluble corn starch, potato starch or soya bean starch, hydroxypropyl cellulose, Merigel SE (starch), Miramist SE (Modified Starch), Promitor L70 (Soluble gluco fibre), Locust Bean Gum (Genu gum), Maltosweet 120 (Maltodextrin), Gellan Gum, Low Acyl (Kelcogel F), Pullulan, Xanthan Gum (Keltrol T) and Pectin (Genu pectin).

Examples of synthetic polymers that may be used include polyethylene glycol. The polyethylene glycol may, for example, have a molecular weight in the range 200-9,500.

As indicated above, the sodium bicarbonate product in accordance with the invention has numerous uses. One of these is as a leavening agent in the production of foodstuffs, for which the product has the particular advantage that it may be used in lower amounts than conventional sodium bicarbonate thus reducing the amount of sodium in the food stuff. For use as a leavening agent, the sodium bicarbonate product may be used either with or without a source of a leavening acid. Thus, for certain applications, the sodium bicarbonate product may be used without a source of a leavening acid, in which case generation of carbon dioxide relies only on heat. In other applications, the sodium bicarbonate product is used in conjunction with a source of a leavening acid so that carbon dioxide is generated by the reaction of these two components.

The sodium bicarbonate product may be formulated into a baking powder which comprises a source of a leavening acid in addition to the sodium bicarbonate product, the leavening acid serving to react with the sodium bicarbonate to generate carbon dioxide.

Therefore, in accordance with a third aspect of the present invention, there is provided a baking powder formulation comprising an admixture of the sodium bicarbonate product of the invention and a source of a leavening acid.

The baking powder formulation in accordance with the invention may, as conventional, also incorporate a storage-enhancing agent which serves to increase the shelf-life of the product. The storage enhancing agent may, for example, be an anti-caking agent as conventionally used in baking powders. The storage enhancing agent may be one that serves to prevent reaction between the sodium bicarbonate product and the source of the leavening acid (the storage enhancing agent effectively serving to "separate" these two components in the powdered form to inhibit reaction and thereby increase shelf life).

The source of leavening acid incorporated in the baking powder formulation in accordance with the third aspect of the invention may be any such source used in conventional baking powders. The source may, for example, be sodium acid pyrophosphate (SAPP), monohydrated calcium pyrophosphate (MCP) anhydrous monocalcium phosphate (AMPC), or sodium aluminium phosphate (SALP).

A baking powder formulation in accordance with the invention may, for example, comprise an admixture of 28% to 32% of the sodium bicarbonate product, 43% to 47% by weight of the source of the leavening acid, and 23% to 27% by weight of a storage enhancing agent.

The storage enhancing agent may, for example, be a low moisture flour.

The sodium bicarbonate product of the invention may be used (with or without a source of a leavening acid as appropriate) for producing cooked food products where leavening is required. Such methods may be entirely conventional and comprise preparing a mix from which the product is to be cooked, the mix incorporating the sodium bicarbonate product, and cooking the mix to produce the foodstuff. Purely by way of example, the cooking may be baking, roasting, grilling, frying or griddling.

However use of the sodium bicarbonate product of the invention (with or without a source of a leavening acid, as appropriate) may be used across the entire spectrum of cooking operations where leavening is required.

By way of a particular example, the sodium bicarbonate product of the invention may be used (ideally in conjunction with a source of a leavening acid such as provided in a baking powder formulation) for the production of baked items, e.g. cakes, muffins etc. For the production of such baked items, the sodium bicarbonate product (e.g. in a baking powder formulation) may be incorporated in a batter, dough or other mix to be baked which is produced using entirely conventional techniques. As an alternative to using a "pre-prepared" baking powder formulation (i.e. comprising an admixture incorporating the sodium bicarbonate product and the source of leavening acid), it is possible to introduce the sodium bicarbonate product and the source of the leavening acid as separate components into the mix. The sodium bicarbonate product of the invention may also be used to substitute all or part of any salt (i.e. sodium chloride) that would normally be included in the recipe. The use of the sodium bicarbonate product of the invention (in place of conventional sodium bicarbonate and possibly also as a substitute for salt) gives rise to baked products which are of lower sodium content than conventional products. It is possible to achieve, for example, a 25% to 50% reduction in sodium whilst still obtaining products with good texture and taste characteristics.

The sodium bicarbonate product in accordance with the invention is prepared from an aqueous composition which contains sodium bicarbonate and the organic material that is soluble in water, both the sodium bicarbonate and the organic material being at least partially dissolved in the aqueous phase. The aqueous composition is subsequently atomised under conditions providing for evaporation of the water from the atomised droplets to produce the particulate sodium bicarbonate product.

The organic material should be one which is per se a solid under ambient temperature conditions. The material should ideally be a solid in the temperature range of 15° C. to 35° C., more preferably 15° C. to 25° C., although it will be appreciated it may also be a solid at temperatures outside these ranges. The organic material is one which is soluble in water, ideally at ambient temperature. Examples of suitable organic materials have been given earlier.

The sodium bicarbonate used for the process is preferably one which (excluding any water of crystallisation) comprises at least 95% by weight of sodium bicarbonate (i.e. is at least 95% by weight pure), more preferably at least 95% and ideally 100% by weight of sodium bicarbonate on the same basis.

The aqueous admixture (from which the sodium bicarbonate product of the invention is produced) comprises both the organic material and the sodium bicarbonate at least partially dissolved in water. The mixture may be a homogenous solution and may be one that is saturated with respect to sodium bicarbonate. Alternatively the aqueous admixture may be a suspension in which there is suspended (i.e. undissolved) sodium bicarbonate. In such a suspension, the aqueous phase may be saturated with respect to sodium bicarbonate. Furthermore, in such a suspension, the organic material will generally be fully dissolved so that the only suspended solids are of sodium bicarbonate. The use of an admixture which comprises a suspension of sodium bicarbonate has advantages in terms of the commercial viability of the process. However, the use of a suspension does lead to a sodium bicarbonate product containing a relatively lower amount of the hollow particles as compared to the use of a solution in which all of the sodium bicarbonate was dissolved. As seen in electron micrographs, the "non-hollow" (i.e. solid) particle may tend to be of a larger size than the hollow particles, although are still of lower size than the sodium bicarbonate from which the aqueous admixture was initially prepared.

The aqueous admixture will generally comprise 0.1 to 70 g (e.g. 0.1 to 40 g, to 50 g or to 60 g) of the organic material per liter of water and may, for example, comprise up to 1000 g of sodium bicarbonate per liter of water. More preferably the aqueous admixture will contain 100 to 1000 g of sodium bicarbonate per liter of water, and even more preferably 400 to 700 g on the same basis.

The amount of the sodium bicarbonate in the aqueous admixture will generally considerably exceed that of the organic material. Typically the weight ratio of the sodium bicarbonate to the organic material in the aqueous admixture will be in the range 5:1 to 50:1, preferably 5:1 to 35:1, more preferably 5:1 to 15:1, and most preferably 8:1 to 12:1.

As indicated above, the sodium bicarbonate product of the invention is produced by atomisation of the aqueous admixture under conditions providing for evaporation of water from the atomised droplets. An elevated temperature may be employed for the evaporation step (e.g. 50° to 100° C., preferably 65° to 75° C.). The evaporation may be effected using a hot air cyclone effect.

The atomisation and evaporation step may be effected using conventional spray drying apparatus, e.g. provided with a rotary atomiser, dual flow atomiser, twin fluid nozzle or high pressure nozzle. For the purposes of producing small batches of the sodium bicarbonate product, a Buchi Mini Spray Dry B-290 is suitable. Niro or Stork industrial dryers may be used for commercial production of the product.

The nature of the product (in terms of particle size range, mean particle size, fraction of hollow particles etc.) may be determined by the nature of the conditions used in the process. Thus, for example, products in which substantially all of the particles are less than 20 µm may be produced on a small scale using a homogenous aqueous admixture and a Buchi Mini Spray Dryer B-290. Products produced using this technique may comprise a relatively high fraction of hollow particles. Alternatively, use of an aqueous admixture which comprises a suspension of sodium bicarbonate spray dried on an industrial scale spray dryer (e.g. a Niro spray dryer) will tend to produce products of larger size and a lower fraction of hollow particles. Other parameters that may be varied to control the nature of the sodium bicarbonate product obtained are the type of atomiser used, the speed of the atomiser, the solid contents of the aqueous admixture, and its flow rate to the spray drying apparatus.

In view of the fact that the method of the invention leads to a product which comprises hollow particles, it will be found that the bulk density of the product will be less than that of the sodium bicarbonate starting material. Typically, the bulk density of the product will be in the range of 80% to 98% of that of the sodium bicarbonate starting material.

For production of the sodium bicarbonate product on an industrial scale (e.g. using a Niro spray dryer) a perfectly satisfactory technique is to prepare an aqueous admixture comprising a suspension of the sodium bicarbonate product (the aqueous phase containing dissolved sodium bicarbonate (possibly at saturation) and dissolved organic material) at ambient temperature, and then to feed the aqueous admixture to the spray dryer.

If however it is desired to prepare sodium bicarbonate product with particles of somewhat smaller size than those that can be prepared on an industrial spray dryer, then we have found a particular technique to be particularly advantageous. This technique comprises the steps of:

(i) preparing a first aqueous solution of a water soluble organic material that is a solid at ambient temperature by a dissolution process effected such that the temperature of the aqueous solution does not exceed 30° C., said aqueous solution containing 0.1 to 40 g of the organic material per liter of water;

(ii) heating the first aqueous solution prepared in step (i) to a temperature in the range 50° to 65° C.;

(iii) preparing a second aqueous solution by dissolving essentially pure sodium bicarbonate (at least 95% by weight pure (excluding any water of crystallisation), more preferably at least 99% and ideally 100% pure on the same basis) into the first aqueous solution from step (ii) in an amount of at least 100 g of sodium bicarbonate per liter of water whilst maintaining the aqueous phase at a temperature of 50° to 65° C.; and (iv) atomising the second aqueous solution and evaporating water from the atomised droplets at a temperature of 50° to 70° C. to produce particles comprised of sodium bicarbonate and the organic material.

The conditions defined for steps (i)-(iii) were found to be required to produce a non-foaming, homogeneous solution containing sufficient sodium bicarbonate without decomposition for subsequent atomisation and evaporation to produce the desired product.

Furthermore, if the temperature of the solution (containing the dissolved organic material and dissolved sodium bicarbonate) falls below 50° C. (before atomisation and evaporation) then sodium bicarbonate will come out of solution and represent a loss of yield of the desired small size product. If the temperature of the admixture is allowed to exceed 65° C. before atomisation and evaporation then there is a danger of decomposition of the bicarbonate to carbonate, thus detracting from the purity of the desired product.

In order to obtain the desired, small sized product from the homogenous solution, the evaporation of water in step (iv) from the atomised droplets should be effected at a temperature of 50 to 70° C. If the temperature is above this limit then there will be significant decomposition of sodium bicarbonate to sodium carbonate, thus detracting from the purity of the product. If below the lower limit then satisfactory drying in the evaporation stage will not be achieved, For the purposes of step (i) of the method, the dissolution step is effected at a temperature such that the aqueous solution does not exceed 30° C. Conveniently, dissolution may be effected at a temperature in the range 15° C. to 30° C., and ideally at ambient temperature so there is no need to provide heat during this step of the process. The (first) aqueous solution produced in step (i) of the process contains 0.1 to 40 g of the organic material per liter of water. In more preferred embodiments of the invention, the first aqueous solution contains 0.1 to 20 g of the organic material on the same basis and even more preferably 8 to 20 g.

In step (ii) of the method, the first aqueous solution is heated to a temperature in the range 50 to 65° C., more preferably 58 to 62° C. and ideally about 60° C.

Step (iii) of the method involves dissolving at least 100 grams of the essentially pure sodium bicarbonate per liter of the (heated) first aqueous solution. More preferably the amount of sodium bicarbonate is 130 to 155 g per liter of the heated (first) solution. During this dissolution step, the aqueous phase is maintained at a temperature of 50° to 65° C., more preferably 58 to 62° C. and ideally about 60° C.

To produce the sodium bicarbonate product, the mixture is atomised under conditions providing for evaporation of the water from the atomised droplets to produce a particulate sodium bicarbonate product as described above. A temperature of 50° to 70° C. is used for evaporation of the water. Temperatures above 70° C. result in undesirable decomposition of the sodium bicarbonate whereas temperatures below 50° C. do not produce adequate drying The evaporation may be effected using a hot air cyclone effect In practice, the temperature within the chamber of the spray drying apparatus may be monitored by measuring the outlet temperature from the chamber, which will be a good approximation (possibly a few degrees lower) to the temperature with the chamber. Best results for step (iv) are achieved using an outlet temperature of 50° to 65° C. The best temperature in this range will be dependent on the type of spray drying apparatus used. Thus, for example, we have achieved excellent results by employing Buchi Mini Spray Dryer B-290 using an outlet temperature from the chamber of 55° C.

It was only by adopting all of the conditions detailed above for the method of the invention that we were able to produce a product in which the purity of the original sodium bicarbonate was retained. In this way, it is possible to use as starting material sodium bicarbonate in its 100% Nacholite crystalline form and produce a product in which 100% of the crystal structure of the original sodium bicarbonate is retained as Nacholite. Furthermore the conditions of the method were required to produce a product providing the physical characteristics and advantageous properties detailed below.

The present invention will be illustrated with reference to the following non-limiting Examples and accompanying drawings, in which:

FIGS. 1(a) and (b) are scanning electron micrographs at ×3000 and ×5000 respectively of the sodium bicarbonate product obtained in accordance with Example 1;

Figure 8A:
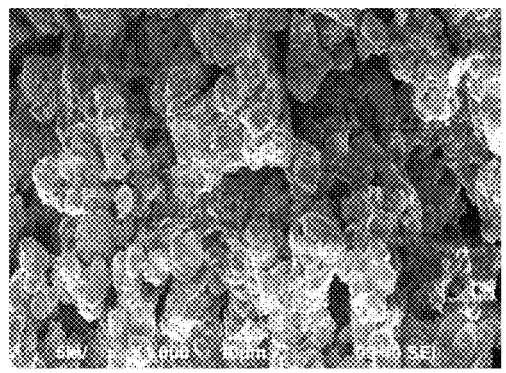
Figure 8B:
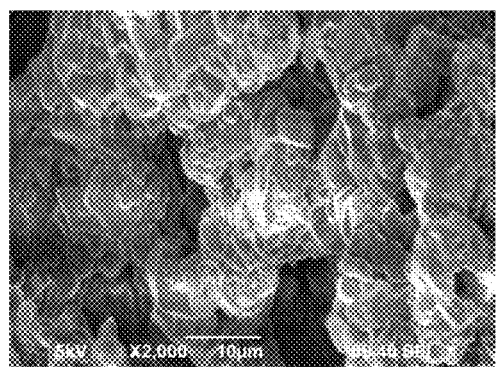
Figure 9:
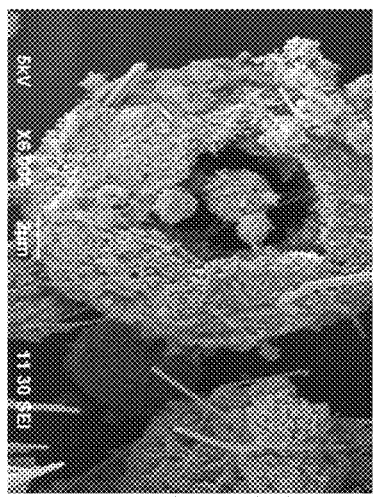
Figure 10:
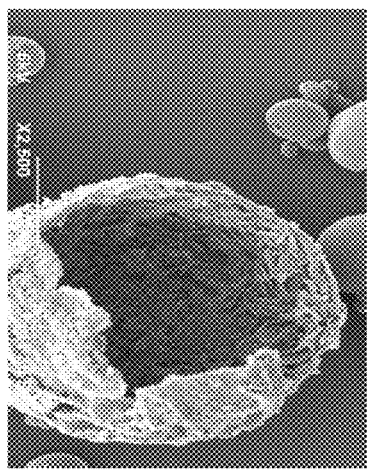
Figure 11:
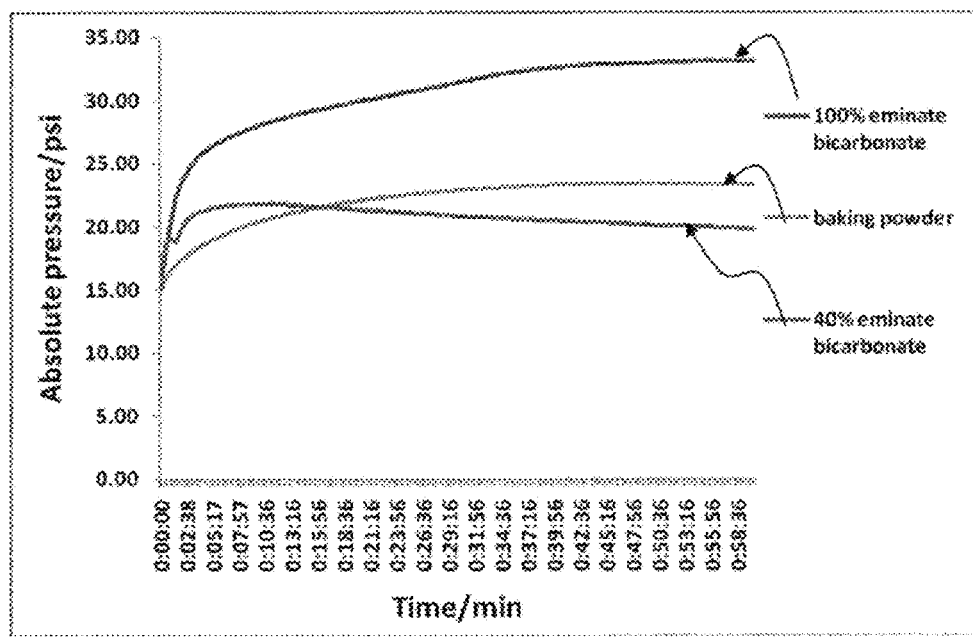
Figure 12:
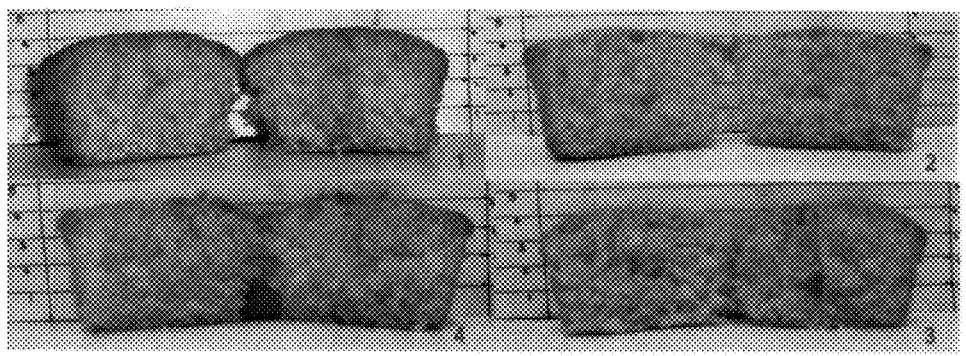

FIGS. 8(a) and (b) are scanning electron micrographs at ×1000 and ×2000 respectively of the potassium bicarbonate product obtained in accordance with Example 4 (Comparative);

FIG. 9 is a scanning electromicrograph at ×6000 of the sodium bicarbonate product obtained in accordance with Example 9;

FIG. 10 is a scanning electromicrograph at ×2500 of the sodium bicarbonate product obtained in accordance with Example 10;

FIG. 11 is a graph showing the result of Example 11 to compare the amounts of carbon dioxide generated by a sodium bicarbonate product in accordance with the invention and a commercially available sodium bicarbonate;

FIG. 12 shows cupcakes obtained in accordance with the procedure of Example 12.

Figure 13:
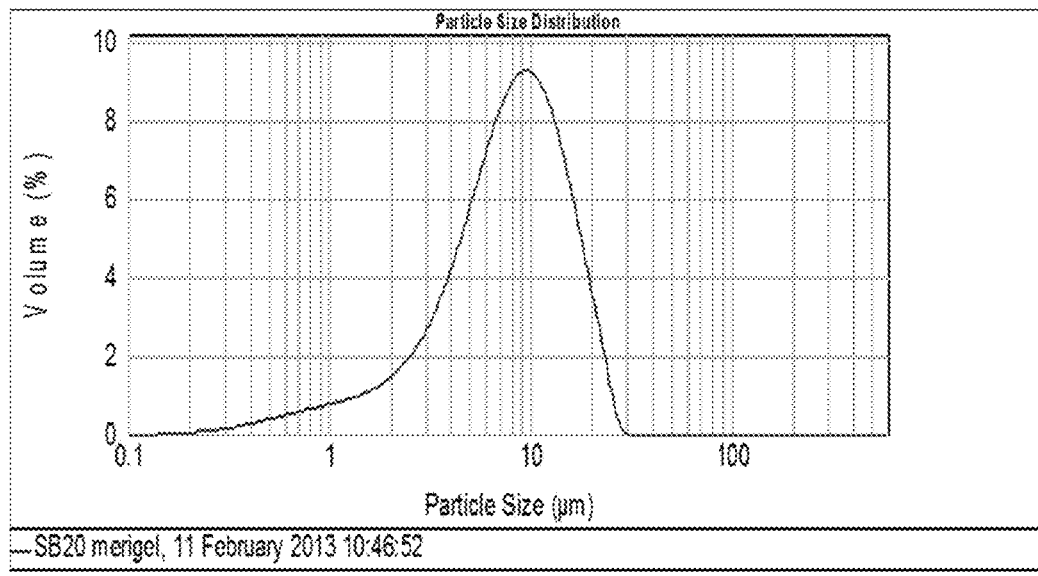
Figure 23:
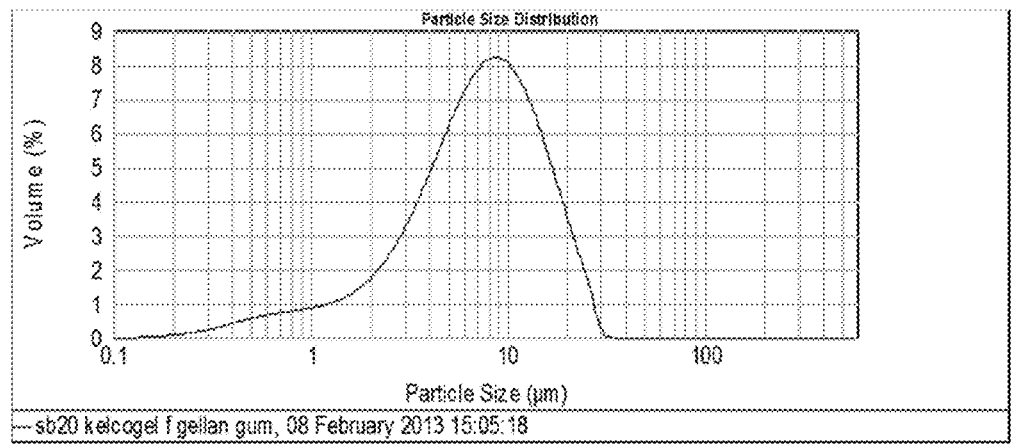
Figure 24:
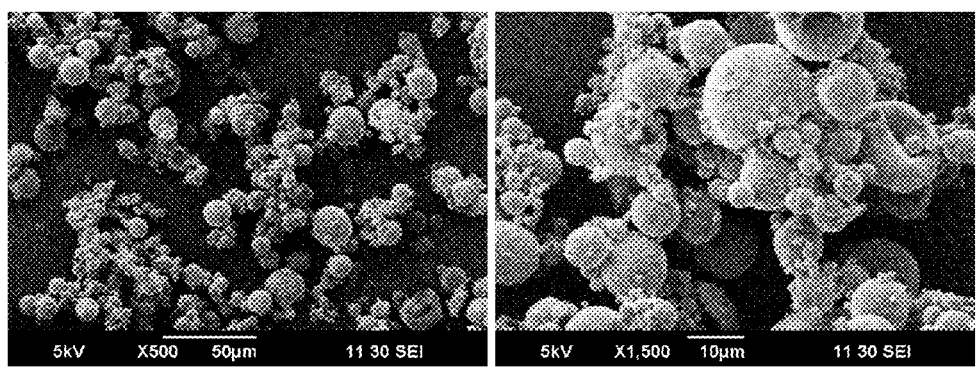
Figure 31:
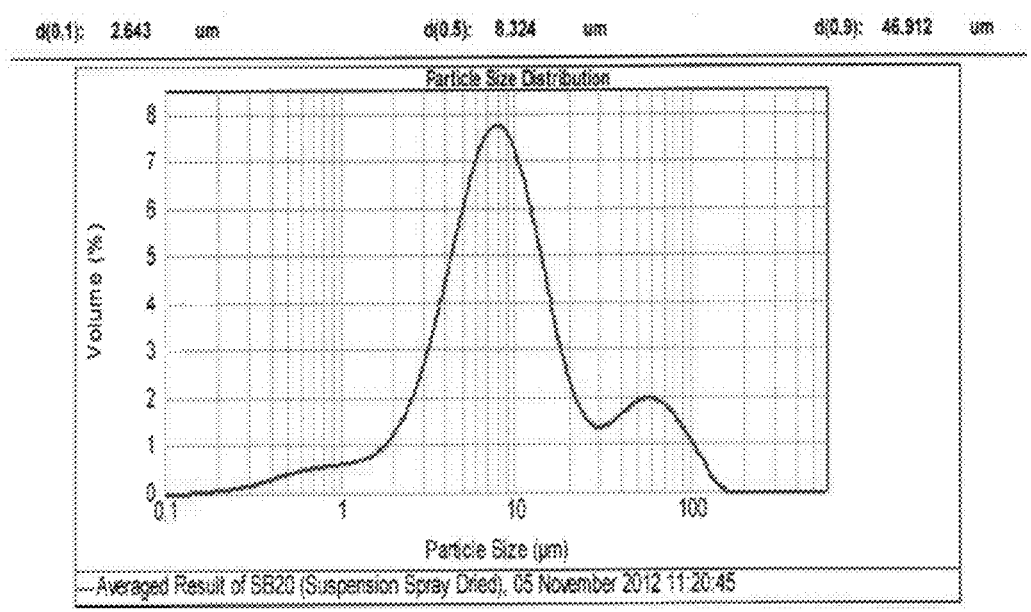
Figure 32:
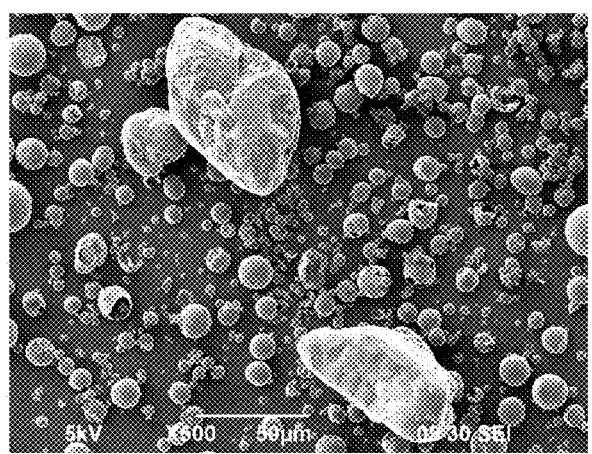
Figure 33:
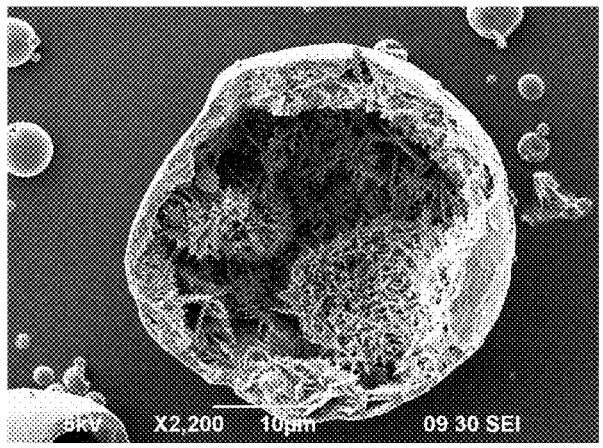
Figure 33:
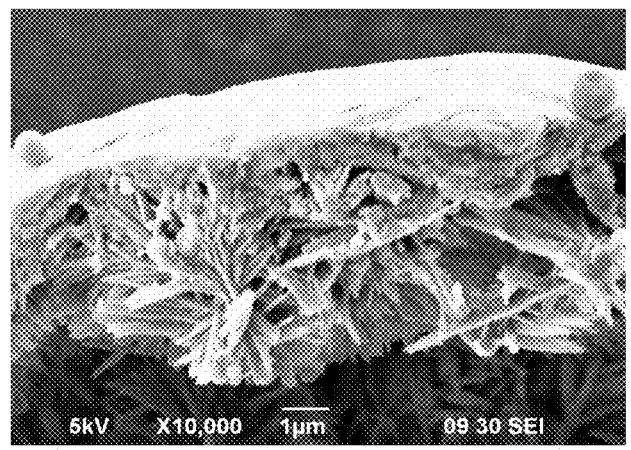
Figure 34A:
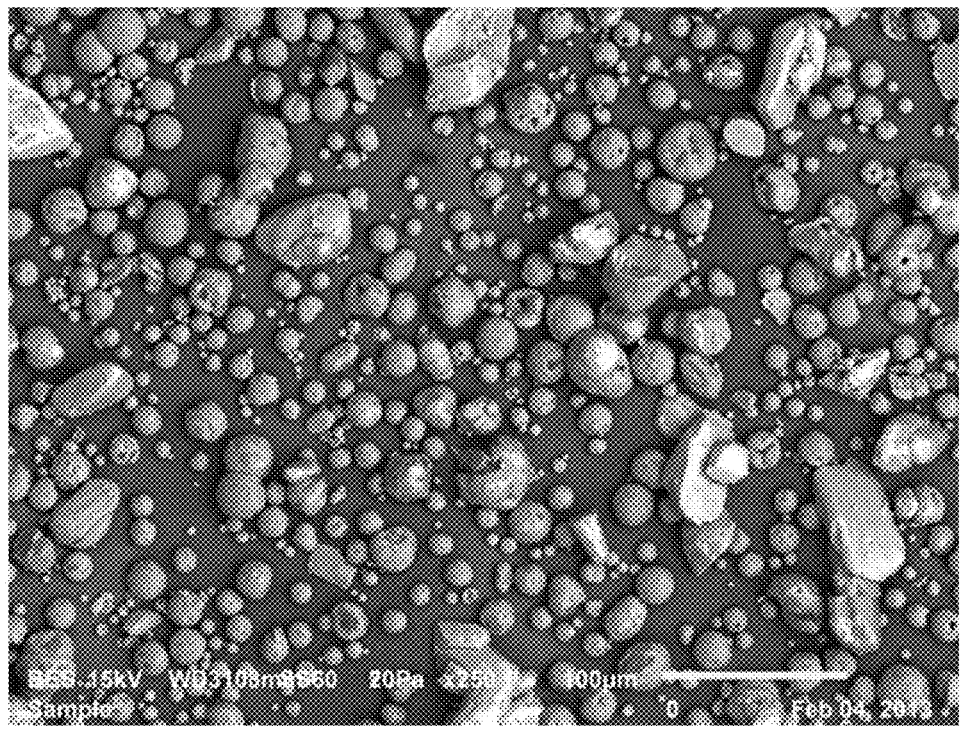
Figure 35:
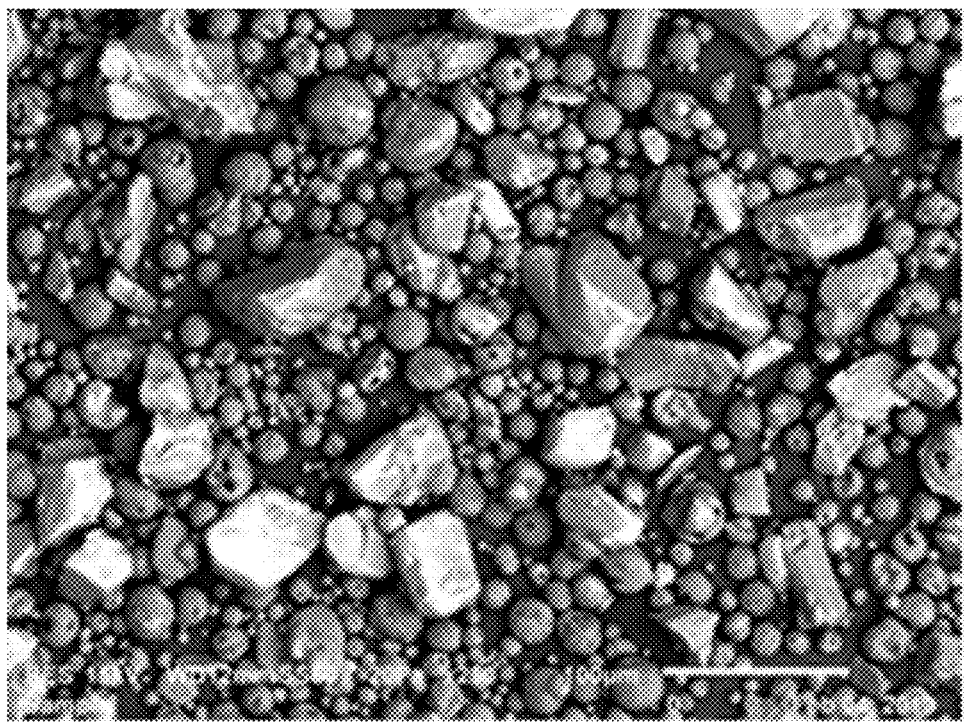
Figure 36:
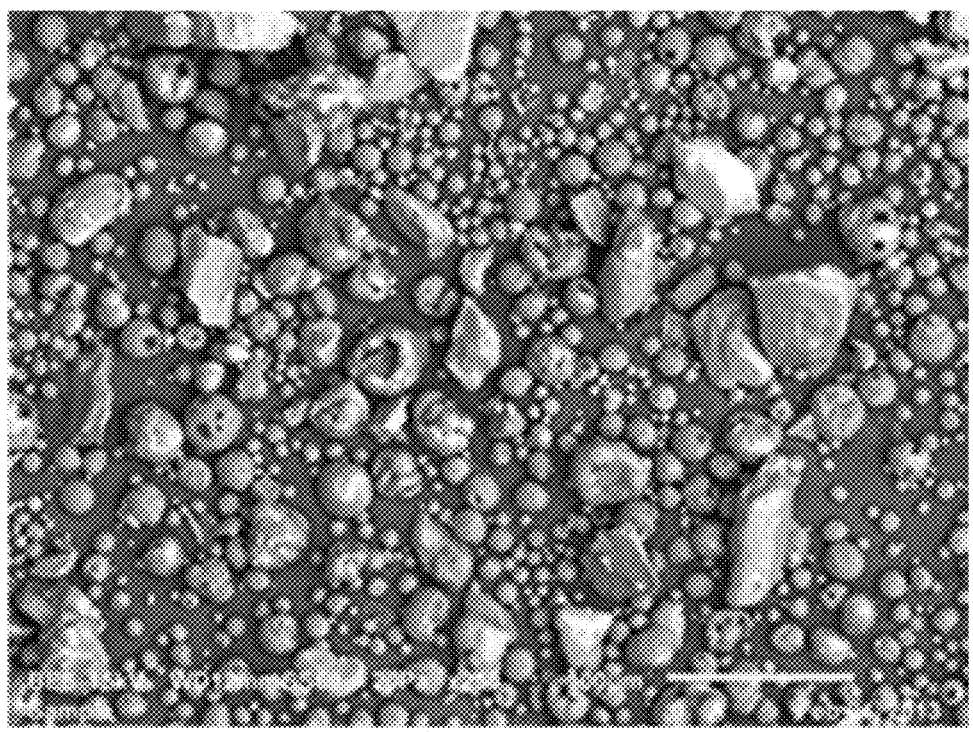
Figure 37:
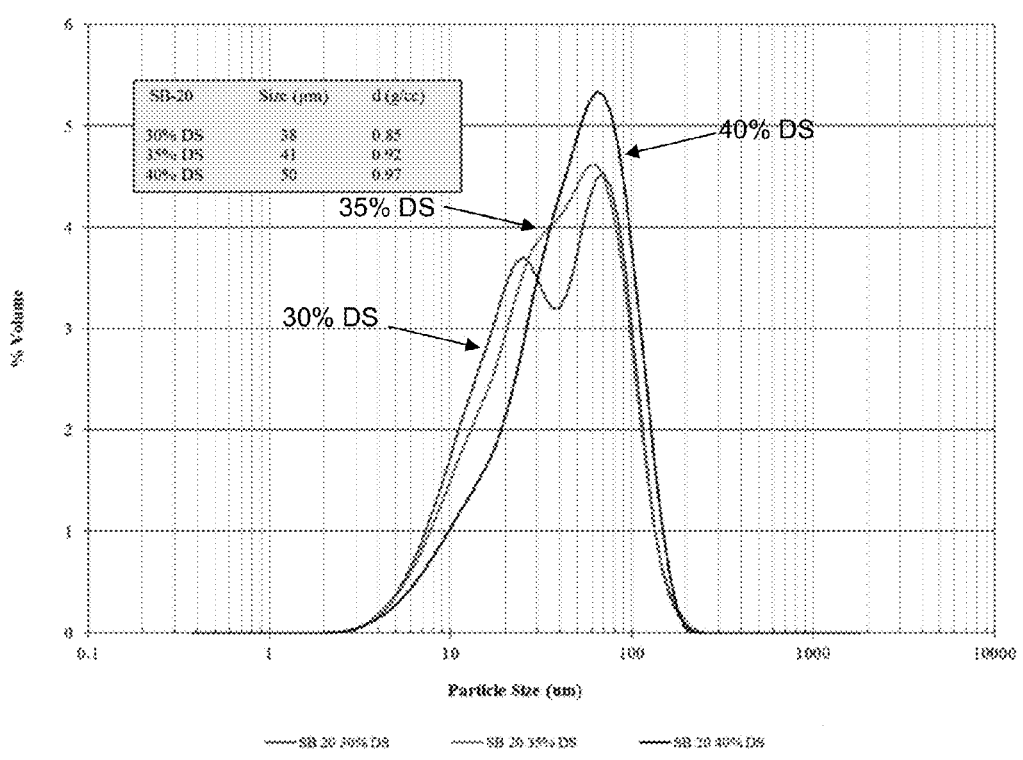
Figure 38:
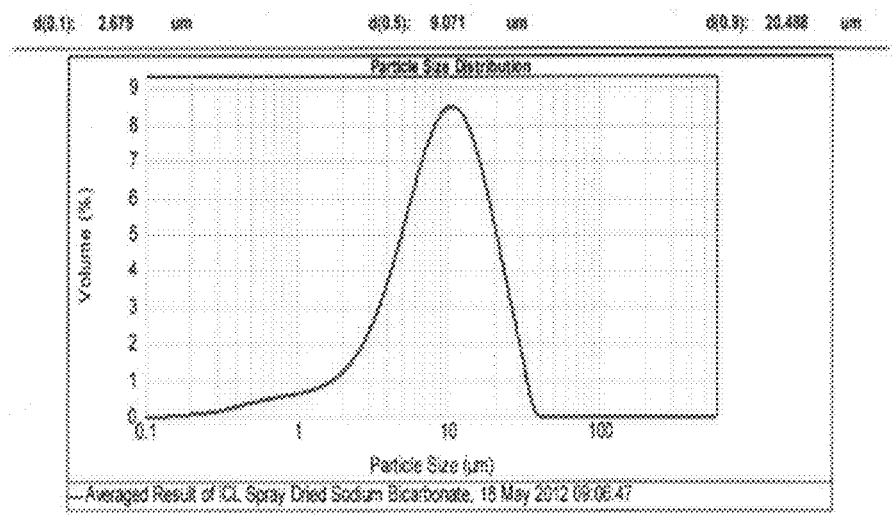
Figure 39:
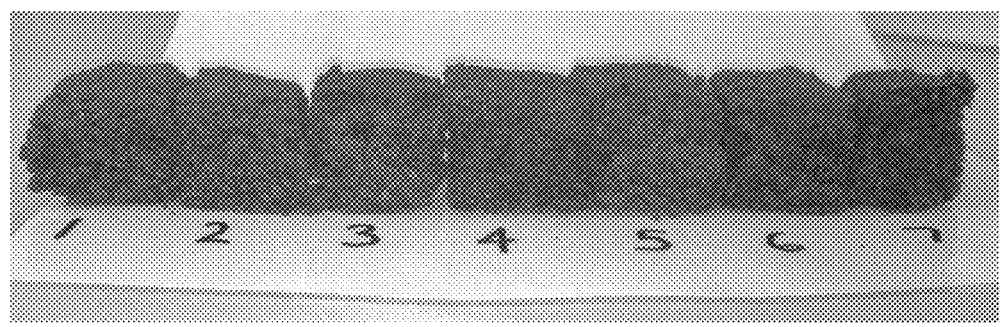
Figure 40A:

FIG. 13 is a particle size distribution for the sodium bicarbonate produced in Example 11;

FIGS. 14(a) and (b) are scanning electron micrographs at magnifications of ×500 and ×1500 of the sodium bicarbonate product produced in Example 11;

FIG. 15 is a particle size distribution for the sodium bicarbonate produced in Example 12;

FIGS. 16(a) and (b) are scanning electron micrographs at magnifications of ×500 and ×1000 of the sodium bicarbonate product produced in Example 12;

FIG. 17 is a particle size distribution for the sodium bicarbonate produced in Example 13;

FIGS. 18(a) and (b) are scanning electron micrographs at magnifications of ×500 and ×1500 of the sodium bicarbonate product produced in Example 13;

FIG. 19 is a particle size distribution for the sodium bicarbonate produced in Example 14;

FIGS. 20(a) and (b) are scanning electron micrographs at magnifications of ×500 and ×1000 of the sodium bicarbonate product produced in Example 14;

FIG. 21 is a particle size distribution for the sodium bicarbonate produced in Example 15;

FIGS. 22(a) and (b) are scanning electron micrographs at magnifications of ×500 and ×1500 of the sodium bicarbonate product produced in Example 15;

FIG. 23 is a particle size distribution for the sodium bicarbonate produced in Example 16;

FIGS. 24(a) and (b) are scanning electron micrographs at magnifications of ×500 and ×1500 of the sodium bicarbonate product produced in Example 16;

FIG. 25 is a particle size distribution for the sodium bicarbonate produced in Example 17;

FIGS. 26(a) and (b) are scanning electron micrographs at magnifications of ×500 and ×1000 of the sodium bicarbonate product produced in Example 17;

FIG. 27 is a particle size distribution for the sodium bicarbonate produced in Example 18;

FIGS. 28(a) and (b) are scanning electron micrographs at magnifications of ×500 and ×1500 of the sodium bicarbonate product produced in Example 18;

FIG. 29 is a particle size distribution for the sodium bicarbonate produced in Example 19;

FIGS. 30(a) and (b) are scanning electron micrographs at magnifications of ×500 and ×1000 of the sodium bicarbonate product produced in Example 19;

FIG. 31 is a particle size distribution for the sodium bicarbonate produced in Example 20;

FIG. 32 are scanning electron micrographs at a magnification of ×500 of the sodium bicarbonate product produced in Example 20;

FIGS. 33(a) and (b) show the internal structure of a hollow particle produced in Example 20 at magnifications of ×2,200 and ×10,000 respectively;

FIGS. 34(a) and (b) are scanning electron micrographs at magnifications of ×250 and ×2,200 respectively of the sodium bicarbonate product produced in Example 21;

FIG. 35 are scanning electron micrographs at a magnification of ×250 respectively of the sodium bicarbonate product produced in Example 22;

FIG. 36 are scanning electron micrographs at a magnification of ×250 respectively of the sodium bicarbonate product produced in Example 23;

FIG. 37 shows particle size distributions for the sodium bicarbonate products produced in accordance with Examples 21 to 23;

FIG. 38 shows the particle size distribution of a sodium bicarbonate product used in Examples 24 to 27 for the production of baked products;

FIG. 39 shows samples of chocolate cake produced in accordance with Example 24; and FIGS. 40(a) and (b) show samples of muffins produced in accordance with Example 26.

Example 1

20 g Instant gum BB (Gum Arabic) were introduced into a 2 Liter conical flask and 2000 ml of deionised water (at ambient temperature) and a magnetic flea added. Stirring was then effected until the Instant gum had dissolved. The conical flask was placed on the hotplate and the solution of Instant gum heated to a temperature of 60° C. with constant agitation.

To the warm solution there were then added 290 g of a commercially available sodium bicarbonate which (by x-ray diffraction) was determined to comprise 100% of Nacholite ($NaHCO_3$) without any amorphous material. Stirring was effected until all of the sodium bicarbonate had been dissolved, whilst maintaining the temperature at 60° C.

The warm solution was then spray dried on a Buchi Mini Spray Dryer B-290 at an inlet temperature of 100 degrees Centigrade and the following settings.

Aspirator %=100
Pump %=40
Air Flow (Height of ball) mm=40
Nozzle Cleaner=3

The "Pump %" value of 40 equates to a temperature of 55° C. just as the product leaves the drying chamber of the Buchi Mini Spray Dryer).

The yield of product from 2 liters was 193.0 gm=62.25%.

Figure 1A:
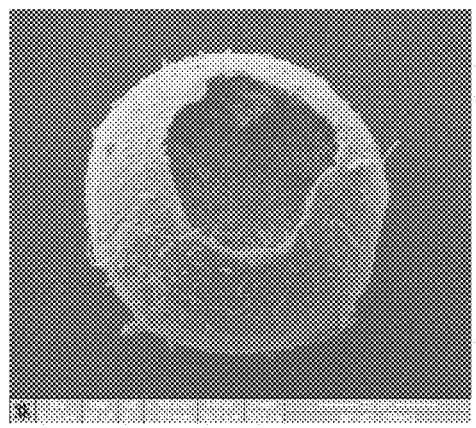

(i) To illustrate the nature of the product obtained, scanning electron micrographs at magnifications of 1000 and 2000 are shown in FIGS. 1(a) and (b) respectively. It can be seen from the figure below that the product comprised substantially spheroidal hollow particles having a size of a few microns.

Figure 2:
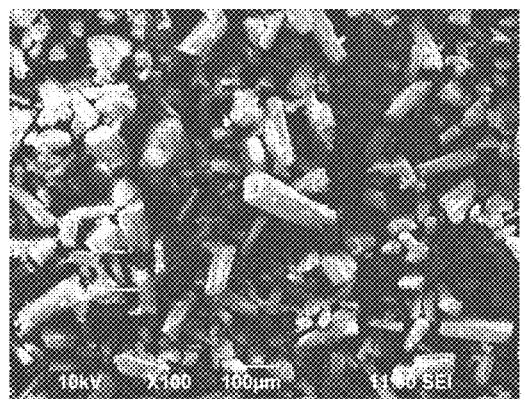
FIG. 2 is a scanning electron micrograph at ×100 of commercially available sodium bicarbonate.
Figure 3:
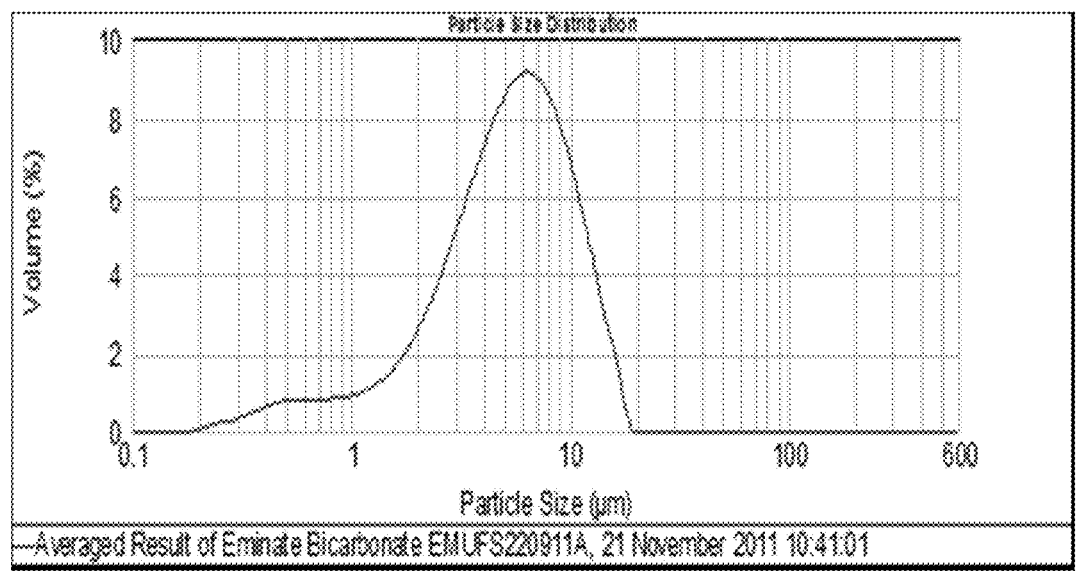
FIG. 3 is a particle size distribution for the sodium bicarbonate produced in Example 1.

The structure of the particles of the product obtained in accordance with this Example may be contrasted with the structure of the crystals present in commercially available sodium bicarbonate, for which a scanning electron micrograph at ×100 is shown in FIG. 2. A comparison of FIG. 1a (magnification ×1000) and FIG. 2 (magnification ×100) shows that the crystals of the commercially available sodium bicarbonate are generally elongate with a length of the order of 100 μm whereas the particle shown in FIG. 1a is generally spherical with a diameter of about 10 μm.

X-ray diffraction analysis of the product showed that it comprised 100% of Nacholite ($NaHCO_3$) without any detectable content of Natron ($Na_2CO_3.10H_2O$) or Natrite ($NaCO_3$).

Example 2

Comparative

The procedure of Example 1 was repeated except that the "Pump %" setting on the Buchi Mini Spray Dryer was set to 30 which equates to a temperature of 85° C. as the product just leaves the drying chamber of the Spray Dryer. This was the setting used in the Examples of WO 2009/133409.

Figure 1B:
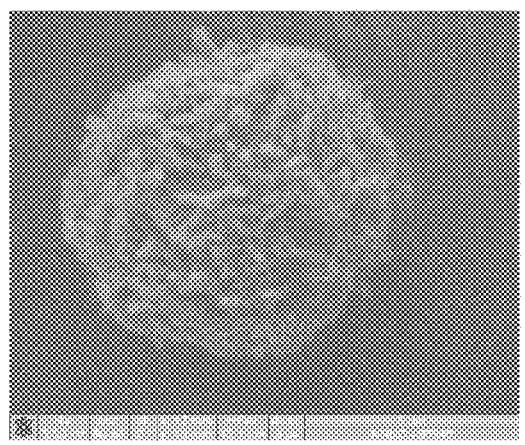
Figure 4:
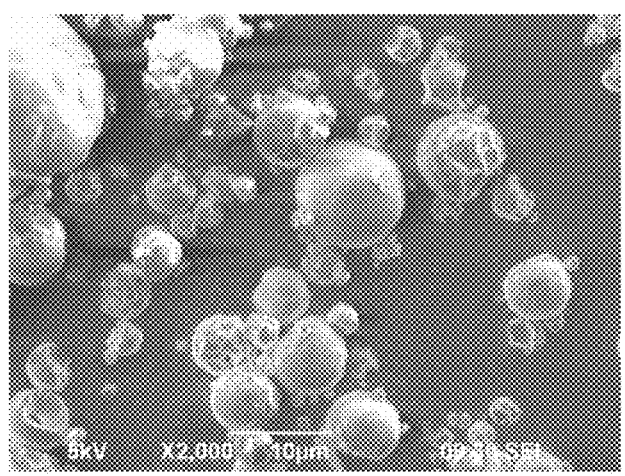
FIG. 4 is a scanning electron micrograph at ×2000 of the product obtained in accordance with Example 2 (comparative)

To illustrate the nature of the product obtained, a scanning electron micrograph at a magnification of ×2000 is shown in FIG. 4. There are two types of particle in this image. The larger smooth spheres are (we believe) comprised substantially sodium carbonate resulting from decomposition of the sodium bicarbonate during the spray drying procedure. Other particles comprise sodium bicarbonate but are of smoother appearance than those shown in FIG. 1 due (we believe) to the presence of sodium bicarbonate in these particles.

Analysis by X-ray diffraction determined that the product comprised 49% by weight of Nacholite and 51% of amorphous material (believed to be sodium carbonate).

Figure 5:
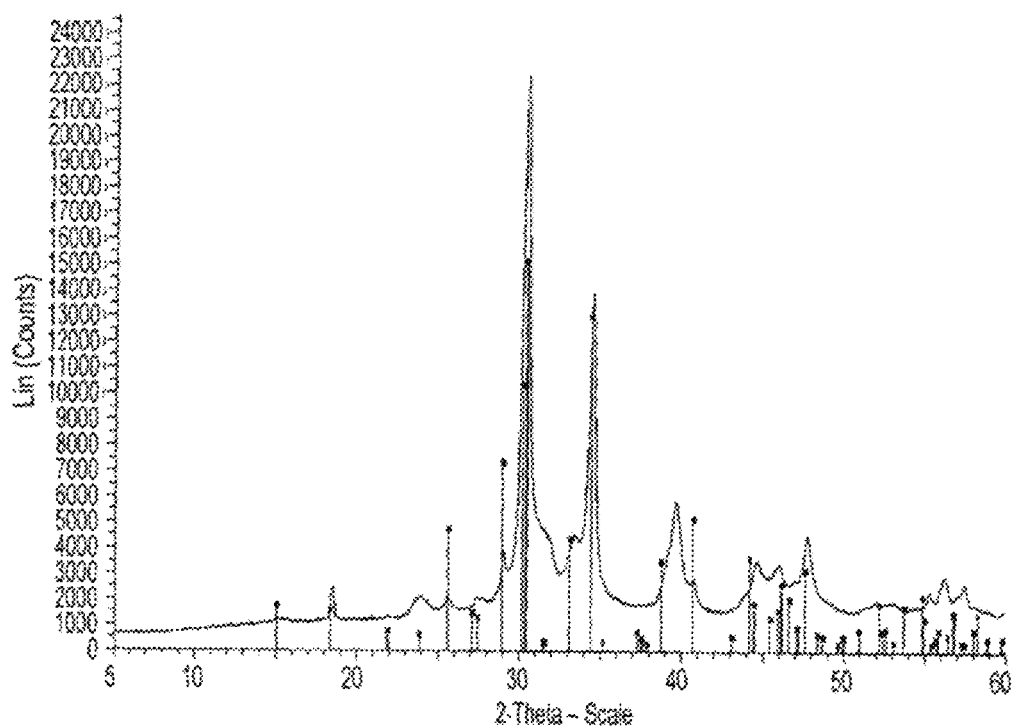
FIG. 5 is an X-ray diffraction spectrum of the product obtained in accordance with Example 2 (comparative)

An X-ray diffraction spectrum of the product is shown in FIG. 5. For the purposes of comparison, an X-ray diffraction spectrum of the original sodium bicarbonate (as received) is shown in FIG. 6.

Figure 6:
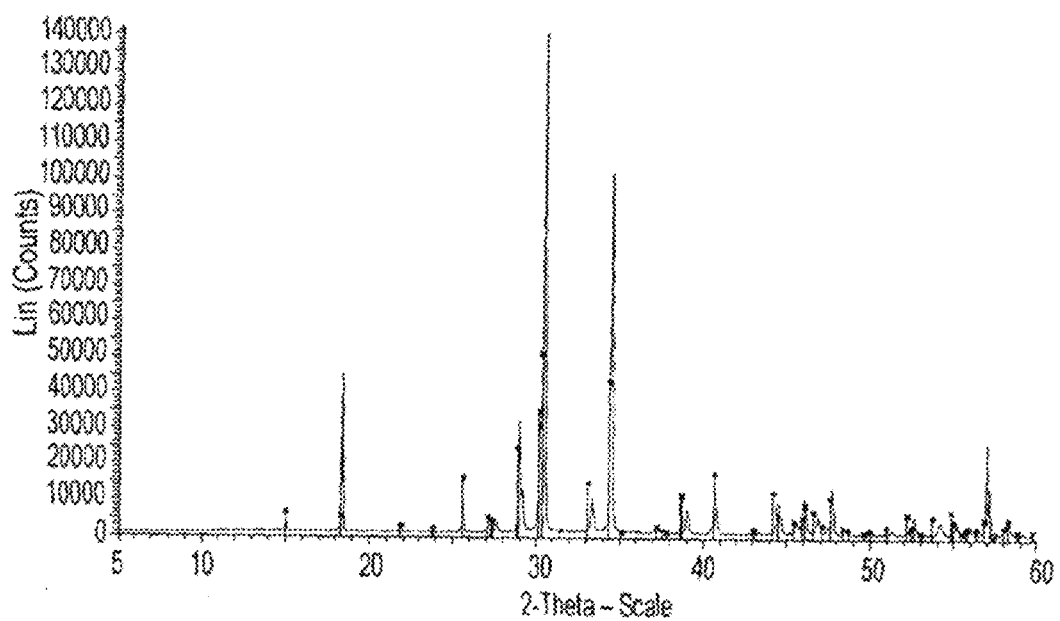
FIG. 6 is an X-ray diffraction spectrum of the sodium bicarbonate starting material used in Example 2 (comparative)

FIG. 6 shows that the original sodium bicarbonate has sharp well presented peaks, indicative of a high degree of crystal order and a large crystallite size (>100 nm). On the other hand, the sample produced in accordance with this Example (spectrum shown in FIG. 5) has considerable peak broadening due to both small crystallite size and residual stress within the sample.

Example 3

Comparative

The procedure of Example 1 was repeated but using sodium carbonate instead of sodium bicarbonate and effecting dissolution of the sodium carbonate at 90° C.

The resulting solution was then spray dried on a Buchi Mini Spray Dry B-290 using the same conditions as employed in Example 1.

This procedure yielded 92.4 g of product, representing a yield of 57.75%.

Figure 7:
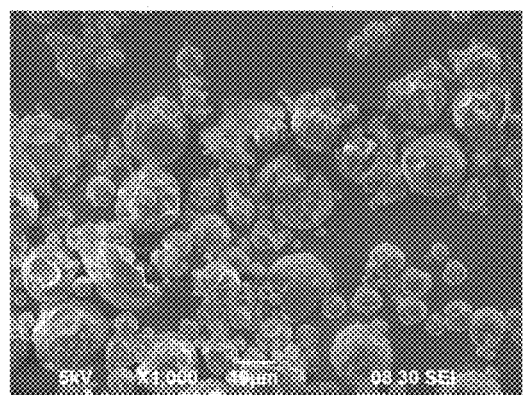
FIG. 7 is a scanning electron micrograph at ×1000 of the sodium carbonate product obtained in accordance with Example 3 (Comparative)

FIG. 7 is a scanning electron micrograph at ×1000 of the product obtained. It can be seen from FIG. 7 that the product produced comprised of roughly spherical balls with a rugged appearance. The balls were solid rather than hollow and have an average particle size of 6 μm.

Example 4

Comparative

This Example demonstrates the spray drying if a solution of potassium bicarbonate and Gum Arabic.

The procedure of Example 1 was repeated but using potassium bicarbonate instead of sodium bicarbonate.

A white powder was produced, for which scanning electron micrographs at ×1000 and ×2000 are shown in FIGS.

8(a) and (b) respectively. As can be seen from these Figures, the powder comprised cube-shaped potassium bicarbonate crystals, in complete contrast to the hollow, generally spherical particles obtained using sodium bicarbonate.

Example 5

Comparative

This Example demonstrates the spray drying if a solution of ammonium bicarbonate and Gum Arabic.

The procedure of Example 4 was repeated but using ammonium bicarbonate in place of potassium bicarbonate.

The ammonium bicarbonate appeared to react in the drying process and the resultant product could not be) dried enough to analyse.

Example 6

Example 1 was repeated but using polyethylene glycol (molecular weight 6000) instead of the Instant gum. A scanning electron micrograph at ×6000 of the product obtained is shown in FIG. 9.

It can be seen that the product had a hollow, ball-like structure.

Example 7

Example 1 was repeated but using maltodextrin instead of the Instant gum. A scanning electron micrograph at ×6000 of the product obtained is shown in FIG. 10.

It can be seen that the product had a hollow, ball-like structure.

Example 8

This Example provides a comparison of carbon dioxide generation from two samples (differing in weight) of sodium bicarbonate as produced in accordance with Example 1 above and a sample of commercially available sodium bicarbonate.

Measurements of carbon dioxide generation were made using an Ankon RFS gas production measurement system.

For the purposes of this Example, measurements of carbon dioxide generation were made using:
 (i) a 2.5 g sample of the product of Example 1 (designated herein as "100% eminate bicarbonate");
 (ii) a 1.0 g sample of the product of Example 1 (designated herein as £40% eminate bicarbonate); and
 (iii) a 2.5 g sample of commercially available sodium bicarbonate (designated herein as "baking powder").

The results of the measurements are shown in FIG. 11. It will been seen from FIG. 11 that the 2.5 g sample of the product of Example 1 (designated in FIG. 11 as "100% eminate bicarbonate") generated the largest volume of carbon dioxide (as measured by absolute pressure). Furthermore, the 1.0 g sample of the product of Example 1 designated in FIG. 11 as "40% eminate bicarbonate" released similar amounts of carbon dioxide as 2.5 g of conventional sodium bicarbonate (designated as "baking powder").

This Example therefore clearly demonstrates the superior ability of the product produced in accordance with Example 1 to produce carbon dioxide as compared to commercially available sodium bicarbonate. The improvement is so large that a sample of the product of Example 1 which was only 40% by weight of the commercially available sodium bicarbonate generated about the same amount of carbon dioxide.

Example 9

Two sets of cupcakes were produced using sodium bicarbonate as a raising agent. These two sets of cupcakes were prepared to the same recipe and using the same baking conditions but one set was prepared using commercially available sodium bicarbonate as raising agent and the other set was prepared using the sodium bicarbonate product of Example 1 of raising agent in an amount of 75% of the commercially available sodium bicarbonate used in preparation of the other set.

Samples of the cupcakes obtained were cut in half and photographs are shown in FIG. 12. In this Figure, four cupcakes are shown and identified by the numbers 1-4. Cupcakes 1 and 2 were prepared using commercially available sodium bicarbonate whereas cupcakes 3 and 4 were prepared using the sodium bicarbonate product of Example 1 as raising agent. The four cupcakes shown in FIG. 12 were all photographed in front of a measurement scale to show the height of the cakes obtained.

It will be seen from FIG. 12 that all cupcakes were of similar height, demonstrating the same evolution of carbon dioxide by both the commercially available sodium bicarbonate and the reduced (75% amount of sodium bicarbonate obtained in accordance with Example 1.

The internal structure of the cupcakes and their taste was also very similar as between those obtained using convention sodium bicarbonate and those obtained using the sodium bicarbonate product of Example 1.

Example 10

The product of Example 1 and commercially available sodium bicarbonate were compared for their antimicrobial activity against *Staphylococcus aureus*, *Pseudomonas aeruginosa*, *Escherichia coli* and *Listeria monocytogenes*. It was found that 1 g of the sodium bicarbonate produced in accordance with Example 1 and 1.5 g of normal sodium bicarbonate provided the same antimicrobial activity, demonstrating that the sodium bicarbonate produced in accordance with the invention can be used in an antimicrobial application at lower levels. This is due to the increased surface area and unique structure of the present invention.

Example 11

3 g Merigel and 200 ml of deionised water (at ambient temperature) were introduced into a 200 ml conical flask and a magnetic flea added. Stirring was then effected until the Merigel had dissolved. The conical flask was placed on a hotplate and the solution heated to a temperature of 60° C. with constant agitation.

To the warm solution there were then added 30 g of a commercially available sodium bicarbonate which (by x-ray diffraction) was determined to comprise 100% of Nacholite ($NaHCO_3$) without any amorphous material. Stirring was effected until all of the sodium bicarbonate had been dissolved, whilst maintaining the temperature at 60° C.

The warm solution was then spray dried on a Buchi Mini Spray Dryer B-290 at an inlet temperature of 100 degrees Centigrade and the following settings.

Aspirator %=100
Pump %=40
Air Flow (Height of ball) mm=40
Nozzle Cleaner=3

The "Pump %" value of 40 equates to a temperature of 55° C. just as the product leaves the drying chamber of the Buchi Mini Spray Dryer).

The particle size distribution of the resultant powders was measured and the results are shown in FIG. 13. Scanning Electron Micrographs of the product at magnifications of 500 and 1500 are shown in FIGS. 14(a) and (b) respectively.

It was determined from the particle size distribution shown in FIG. 13, that the product had the following particle size characteristics:

| D(0.1) = 2.3 µm | D(0.5) = 7.9 µm | D(0.9) = 16.6 µm |

Where
D(0.1) is the size of particle below which 10% by volume of the sample lies
D(0.1) is the size of particle which 50% by volume is smaller and 50% larger
D(0.1) is the size of particle below which 90% by volume of the sample lies.

Figure 14:
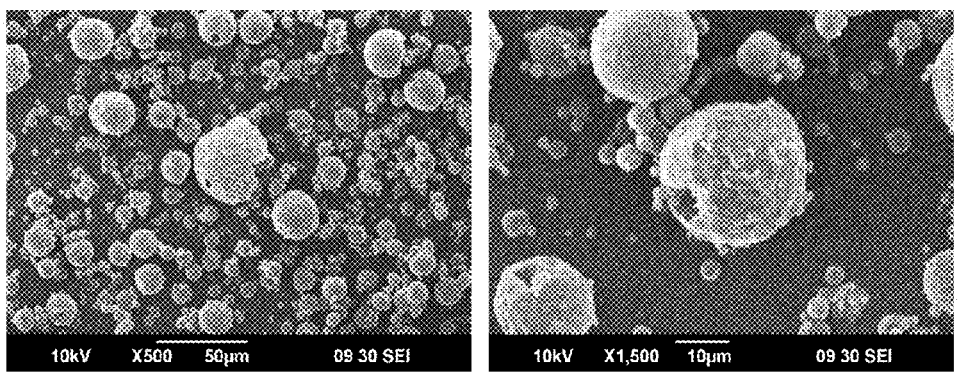

As can be seen from FIG. 14, the product comprised hollow particles (see particularly FIG. 14(b)).

Example 12

The procedure of Example 11 was repeated but using Miramist SE (Modified Starch) instead of Merigel.

The particle size distribution of the resultant product is shown in FIG. 15 and scanning Electron Micrographs at magnifications of 500 and 1000 are shown in FIGS. 16(a) and (b) respectively.

The product had the following particle size characteristics:

| D(0.1) = 1.9 µm | D(0.5) = 6.4 µm | D(0.9) = 13.18 µm |

As shown in FIGS. 16(a) and (b), the product comprised hollow particles (see particularly FIG. 16 (b)).

Example 13

The procedure of Example 11 was repeated but using Promitor L70 (Soluble gluco fibre) instead of Merigel.

The particle size distribution of the resultant product is shown in FIG. 17 and scanning Electron Micrographs at magnifications of 500 and 1500 are shown in FIGS. 18(a) and (b) respectively.

The product had the following particle size characteristics:

| D(0.1) = 1.5 µm | D(0.5) = 5.3 µm | D(0.9) = 11.0 µm |

As shown in FIGS. 18(a) and (b), the product comprised hollow particles (see particularly FIG. 18 (b)).

Example 14

The procedure of Example 11 was repeated but using Locust Bean Gum (Genu gum) instead of Merigel The particle size distribution of the resultant product is shown in FIG. 19 and scanning Electron Micrographs at magnifications of 500 and 1000 are shown in FIGS. 20(a) and (b) respectively.

The product had the following particle size characteristics:

| D(0.1) = 2.5 µm | D(0.5) = 7.9 µm | D(0.9) = 17.1 µm |

As shown in FIGS. 20(a) and (b), the product comprised hollow particles (see particularly FIG. 20 (b)).

Example 15

The procedure of Example A was repeated but using Maltosweet 120 (Maltodextrin) instead of Merigel The particle size distribution of the resultant product is shown in FIG. 21 and scanning Electron Micrographs at magnifications of 500 and 1500 are shown in FIGS. 22(a) and (b) respectively.

The product had the following particle size characteristics:

| D(0.1) = 1.7 µm | D(0.5) = 6.2 µm | D(0.9) = 12.8 µm |

As shown in FIGS. 22(a) and (b), the product comprised hollow particles (see particularly FIG. 22 (b)).

Example 16

The procedure of Example 11 was repeated but using Gellan Gum, Low Acyl (Kelcogel F) instead of Merigel The particle size distribution of the resultant product is shown in FIG. 23 and scanning Electron Micrographs at magnifications of 500 and 1500 are shown in FIGS. 24(a) and (b) respectively.

The product had the following particle size characteristics:

| D(0.1) = 1.9 µm | D(0.5) = 7.3 µm | D(0.9) = 16.9 µm |

Example 17

The procedure of Example 11 was repeated but using Pullulan instead of Merigel

The particle size distribution of the resultant product is shown in FIG. 25 and scanning Electron Micrographs at magnifications of 500 and 1000 are shown in FIGS. 26(a) and (b) respectively.

The product had the following particle size characteristics:

| D(0.1) = 2.6 µm | D(0.5) = 8.0 µm | D(0.9) = 16.4 µm |

Example 18

The procedure of Example 11 was repeated but using Pectin (Genu pectin) instead of Merigel The particle size distribution of the resultant product is shown in FIG. 27 and scanning Electron Micrographs at magnifications of 500 and 1500 are shown in FIGS. 28(a) and (b) respectively.

The product had the following particle size characteristics:

| D(0.1) = 2.1 μm | D(0.5) = 6.9 μm | D(0.9) = 13.9 μm |

As shown in FIGS. 28(a) and (b), the product comprised hollow particles (see particularly FIG. 28 (b)).

Example 19

The procedure of Example 11 was repeated but using Xanthan Gum (Keltrol T) instead of Merigel.
The particle size distribution of the resultant product is shown in FIG. 29 and scanning Electron Micrographs at magnifications of 500 and 1500 are shown in FIGS. 30(a) and (b) respectively.
The product had the following particle size characteristics:

| D(0.1) = 2.5 μm | D(0.5) = 7.0 μm | D(0.9) = 14.4 μm |

The particles produced are 5-10 μm and appear to be hollow.

Example 20

3 g Gum Arabic and 100 ml of deionised water (at ambient temperature) were introduced into a 200 ml conical flask and a magnetic flea added. Stirring was then effected until the Gum Arabic had dissolved. The conical flask was placed on a hotplate and the solution heated to a temperature of 60° C. with constant agitation.
To the warm solution there were then added 30 g of a commercially available sodium bicarbonate which (by x-ray diffraction) was determined to comprise 100% of Nacholite (NaHCO$_3$) without any amorphous material. Stirring was effected until no more sodium bicarbonate dissolved, whilst maintaining the temperature at 60° C. As a result of this procedure, a suspension of sodium bicarbonate was obtained.
The warm suspension was then spray dried (while stirring) on a Buchi Mini Spray Dryer B-290 using the same settings as in Example 11.
A white free-flowing powder was produced.
The particle size distribution of the powder is shown in FIG. 31 and a SEM image at a magnification of 500 is shown in FIG. 32. The product had the following particle size characteristics:

| D(0.1) = 2.643 μm | D(0.5) = 8.324 μm | D(0.9) = 46.912 μm |

It will be seen from FIGS. 31 and 32 that there are two types of particles present. More particularly, there were small particles with a size around 7-10 μm and larger particles with a size around 50 μm. The different size particles are clearly seen in FIG. 32. Additionally, FIG. 31 shows that the product had a bimodal particle size distribution with the "major peak" centred on a particle size of about 7-9 μm (representing nearly 80% of the product) and a "minor peak" centred on about 50 μm.
FIGS. 33(a) and (b) show the internal structure of one of the "small particles" at magnifications of 2200 and 10000 respectively. The particle is seen to be hollow with sodium bicarbonate crystals on the inside and a Gum Arabic coating on the outside.
It is hypothesised that the larger particles are not hollow and there is no evidence of a hollow structure from SEM images. Without wishing to be bound by theory, we believe that the larger particles were not fully dissolved before spray drying. The particles were however smaller than the starting sodium bicarbonate (cf FIG. 2). It is therefore presumed that sodium bicarbonate had been dissolved from the surface of the original particles (thereby reducing their size), which supports the theory that they have not fully dissolved.

Example 21

11.34 kg of MilliQ water was weighed into a clean, dry approx 20 liter bucket. 2.27 kg of NaHCO$_3$ was then added to the bucket with stirring (using an overhead stirrer and impeller). 0.5 kg of InstantGum BB (acacia gum) was added and stirring continued for 10 minutes. A further 2.81 kg of NaHCO$_3$ (loose bulk density 1.00 g/cc) was added with stirring to the slurry which was then stirred for an additional 10 minutes.
The solution was then poured through a 595 μm sieve into another clean, dry bucket. Additional water was required to rinse the bucket and sieve. The total solution weight after rinsing and sieving was 18.77 kg (29.7% solids).
Spray Drying of the suspension was performed on a small NIRO Utility Dryer Model V Spray Dryer equipped with a rotary atomizer and cyclonic separator.
With the dryer completely assembled, the Niro fan and atomizer motor were started. The heater was started and the set point was set to 200° C. Dryer conditions and set points are shown in Table 1.
The slurry was stirred throughout manufacturing to keep the NaHCO$_3$ suspended in the solution during feeding of the dryer.

TABLE 1

| Time | Inlet T (C.) | Outlet T (C.) | Pump Speed (mL/min) | Notes |
|---|---|---|---|---|
| 2:25 | — | — | — | Ran 1.89 liters of 200 ppm bleach through dryer to sanitize. Rinsed w/ 1.89 liters of water. |
| 2:35 | 20 | 24 | 0 | Turned on heat. |
| 3:15 | 200 | 157 | 200 | Started water feed. |
| 3:25 | 200 | 93 | 250 | Switched to NaHCO$_3$ feed (30% ds, Example 21). |
| 3:35 | 200 | 88 | 250 | Collected sample. |
| 3:55 | 200 | 88 | 250 | ½ way through bucket. |
| 4:15 | 200 | 91 | 250 | nearing bottom of bucket. |
| 4:30 | 200 | 82 | 250 | Finished bucket, switched back to water feed. 0.39 kg of solution was left in the bucket. Final weight - 4.97 kg. |
| 4:35 | 200 | 82 | 450 | Increased pump speed to cool dryer. |

Figure 34B:
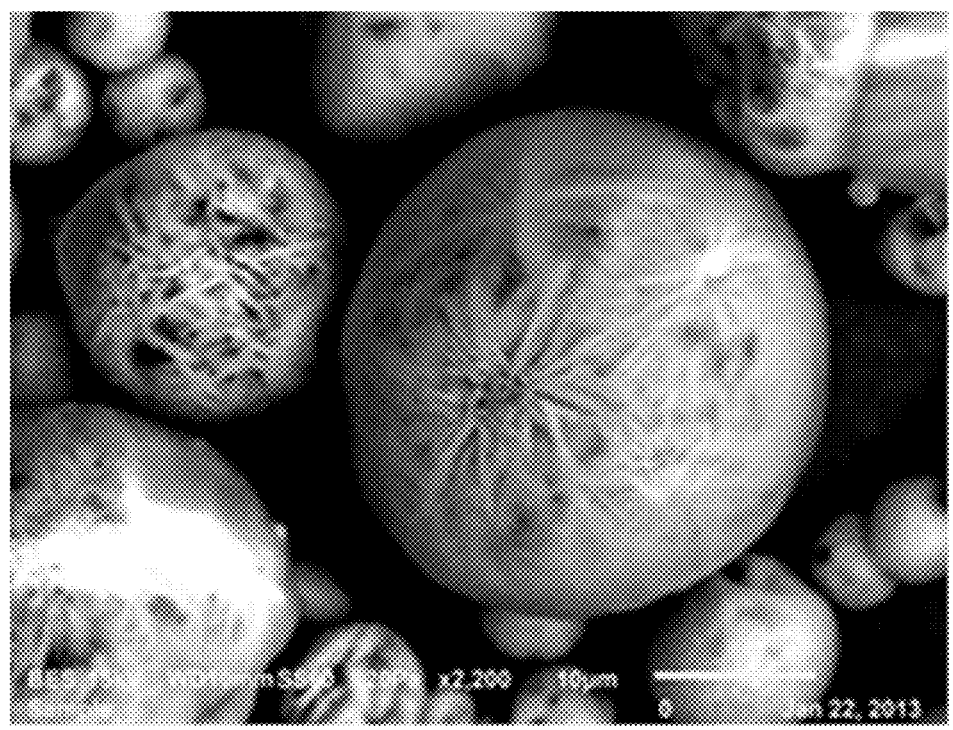

Dry samples were examined using Scanning Electron Microscopy and the images are shown in FIG. 34. At 30% solids the resultant product consists of both hollow spheres and some larger undissolved particles. Loose bulk density and particle size distribution were also tested and the results are shown in FIG. 37.
The loose bulk density was found to be 0.85 g/cc.
This data indicates that at 30% solids the resultant product contains ~½ hollow spheres and ½ undissolved particles.

Example 22

7.7 kg of MilliQ water was weighed into a clean, dry approx 20 liter bucket. 2.27 kg of NaHCO$_3$ was then added to the bucket with stirring (using an overhead stirrer and impeller). 0.57 kg of InstantGum BB (acacia gum) was added and stirring continued for 10 minutes. A further 3.51 kg of NaHCO$_3$ (loose bulk density 1.00 g/cc) was added with stirring to the slurry which was then stirred for an additional 10 minutes.

The solution was then poured through a 595 μm sieve into another clean, dry bucket. 4.08 kg of MilliQ water was used to rinse the bucket and sieve. The total solution weight after rinsing and sieving was 18.14 kg (35% solids).

Spray Drying of the suspension was performed on a small NIRO Utility Dryer Model V Spray Dryer equipped with a rotary atomizer and cyclonic separator.

With the dryer completely assembled, the Niro fan and atomizer motor were started. The heater was started and the set point was set to 200° C. Dryer conditions and set points are shown in Table 2.

The slurry was stirred throughout manufacturing to keep the NaHCO$_3$ suspended in the solution during feeding of the dryer.

TABLE 2

| Time | Inlet T (C.) | Outlet T (C.) | Pump Speed (mL/min) | Notes |
|---|---|---|---|---|
| 11:00 | — | — | — | Ran 1.89 liters of 200 ppm bleach through dryer to sanitize. Rinsed w/ 1.89 liters of water. |
| 1:40 | 200 | 24 | 0 | Turned on heat. |
| 2:10 | 200 | 143 | 200 | Started water feed. |
| 2:15 | 200 | 93 | 300 | Switched to NaHCO$_3$ feed (35% ds, Example 22). |
| 2:30 | 200 | 79 | 300 | Took first sample. |
| 2:50 | 200 | 82 | 300 | Took Sample. |
| 3:05 | 200 | 85 | 200 | Finished bucket, switched back to water feed. Final weight - 5.53 kg. |

Dry samples were examined using Scanning Electron Microscopy and an image from this is shown in FIG. 35. At 35% solids the resultant product consists of both hollow spheres and some larger undissolved particles. Loose bulk density and particle size distribution were also tested and the results are shown in FIG. 37.

The loose bulk density was found to be 0.92 g/cc.

This data indicates that at 35% solids there is an increase in undissolved particles when compared to Example 21.

Example 23

7.71 kg of MilliQ water was weighed into a clean, dry approx 20 liter bucket. 2.27 kg of NaHCO$_3$ was then added to the bucket with stirring (using an overhead stirrer and impeller). 0.65 kg of InstantGum BB (acacia gum) was and stirring continued for 10 minutes. A further 4.34 kg of NaHCO$_3$ (loose bulk density 1.00 g/cc) was added with stirring to the slurry which was then stirred for an additional 10 minutes.

The solution was then poured through a 595 μm sieve into another clean, dry bucket. The remaining 3.18 kg of MilliQ water was used to rinse the bucket and sieve. The total solution weight after rinsing and sieving was 18.14 kg (40% solids).

Spray Drying of the suspension was performed on a small NIRO Utility Dryer Model V Spray Dryer equipped with a rotary atomizer and cyclonic separator.

With the dryer completely assembled, the Niro fan and atomizer motor were started. The heater was started and the set point was set to 200° C. Dryer conditions and set points are shown in Table 3.

The slurry was stirred throughout manufacturing to keep the NaHCO$_3$ suspended in the solution during feeding of the dryer.

TABLE 3

| Time | Inlet T (C.) | Outlet T (C.) | Pump Speed (mL/min) | Notes |
|---|---|---|---|---|
| 3:10 | 200 | 88 | 350 | Switched to NaHCO$_3$ feed (40% ds, Example 25). |
| 3:15 | 200 | 66 | 330 | Reduced pump speed. |
| 3:25 | 200 | 66 | 330 | Took first sample. |
| 3:40 | 200 | 71 | 330 | Took Sample. |
| 3:45 | 200 | 71 | 330 | Finished bucket, switched back to water feed. Final weight - 6.03 kg (0.82 kg solution was left in bucket). |
| 3:50 | 200 | 66 | 500 | Increased pump speed to cool dryer. |

Dry samples were examined using Scanning Electron Microscopy and an image from this is shown in FIG. 36. At 40% solids the resultant product consists of both hollow spheres and some larger undissolved particles. Loose bulk density and particle size distribution were also tested and the results are shown in FIG. 37.

The loose bulk density was 0.97 g/cc.

This data indicates that at 40% solids there is an even greater increase in undissolved particles when compared to Examples 21 and 22.

Example 24

This Example demonstrates production of chocolate cake using baking powders containing sodium bicarbonate in accordance with the invention and, for the purposes of comparison, a conventional (commercially available) baking powder containing standard sodium bicarbonate. More particularly, the Example demonstrates successful production of chocolate cake using baking powders containing sodium bicarbonate in accordance with the invention and containing reduced amounts of sodium as compared to the chocolate incorporating the conventional baking powder.

The sodium bicarbonate product in accordance with the invention used for the purpose of this Example was produced using a Niro spray dryer with a feed temperature of 50° C., an inlet of 150° C. and an exhaust of 65° C. The product has a particle size distribution as shown in FIG. 38 and is designated herein as SB20.

Table 1 below shows the recipe (Recipe No. 1) used with the conventional baking powder (which comprised about 28% by weight of sodium bicarbonate, about 33% low moisture flour and about 39% SAPP (sodium acid pyrophosphate). The compositions of the baking powders (and amounts thereof) incorporating sodium bicarbonate in accordance with the invention are detailed below.

TABLE 4

(Recipe No. 1)

| Ingredients | % |
|---|---|
| Sugar | 31.80% |
| Margarine | 23.10% |
| Wheat flour T55 | 17.25% |
| Hot Water | 10.00% |
| Water | 8.00% |
| Cocoa powder | 5.00% |
| Pasteurized egg yolk | 1.80% |
| *Vanilla* flavour | 1.00% |
| Pasteurized egg albumen | 0.85% |
| Baking powder | 0.80% |
| Salt | 0.20% |
| Potassium sorbate | 0.20% |
| Total | 100.00% |

As indicated above, chocolate cake was also produced to variations of the above recipe using a baking powder containing 30% by weight of the SB20, 45% by weight SAPP and 25% by weight of low moisture flour.

The variations are shown as Recipes Nos. 2-7 in Table 5 below. (Which for convenience also includes Recipe No. 1).

For convenience, this baking powder composition (incorporating the SB20 product of the invention) is referred to in this example as Eminate Baking Powder.

TABLE 5

| Recipe No. | Details |
|---|---|
| 1 | As per Table 1 |
| 2 | 25% reduction in the % of baking powder and use Eminate Baking Powder |
| 3 | 25% reduction in the % of baking powder and use Eminate Baking Powder AND remove all added salt from recipe |
| 4 | 25% reduction in the % of baking powder and use Eminate Baking Powder, remove all added salt from recipe and replace with 75% (by weight) SB20 |
| 5 | 35% reduction in the % of baking powder using Eminate Baking Powder [salt remained in recipe] |
| 6 | 35% reduction in the % of baking powder using Eminate Baking Powder, remove all added salt from recipe and replace with 65% (by weight) SB20 |
| 7 | 50% reduction in the % of baking powder using Eminate Baking Powder, remove all added salt from recipe and replace with 50% (by weight) SB20 |

Recipes Nos. 2-7 were made up of an additional amount of Wheat Flour T55 to ensure consistency of weight with Recipe No. 1.

All of the chocolate cakes were produced using the following procedure.
1. Dissolve egg powders in water.
2. Heat the water and add the cocoa powder.
3. Allow this chocolate preparation cool to room temperature.
4. Sieve dry ingredients.
5. Cream the margarine with the sweeteners (Kenwood mixer: speed 33 2-3 minutes).
6. Add egg preparation and mix (speed 1, 1 minute, then speed 3, 2 minutes).
7. Add dried ingredients and mix (speed 1, 1 minute, then speed 3, 2 minutes).
8. Add the chocolate preparation and mix until obtaining a homogenous batter.
9. Put the batter in cake mould (350 g) and bake at 180° C. for 40 min.

Samples of the chocolate cakes were photographed and the results are shown in FIG. 39 (in which each sample is associated with its Recipe No. shown in Table 5 above).

All of the chocolate cakes were measured for height and also analysed for % ge moisture content, pH and water activity and the results are shown in Table 6 which also includes the % ge sodium content of the cakes and also (in the case of Recipe Nos. 2-7) the % ge reduction in sodium as compared to Recipe No. 1.

TABLE 6

| Recipe No. | Sodium content % | Sodium reduction/% | Height/mm | Moisture content/% | pH | Water activity |
|---|---|---|---|---|---|---|
| 1 | 0.232 |  | 28 | 19.3 | 6.76 | 0.7655 |
| 2 | 0.216 | 7 | 32 | 16.1 | 6.67 | 0.7389 |
| 3 | 0.153 | 35 | 30 | 19.1 | 6.76 | 0.7961 |
| 4 | 0.184 | 21 | 40 | 15.9 | 7.22 | 0.7399 |
| 5 | 0.207 | 11 | 43 | 15.9 | 6.55 | 0.7982 |
| 6 | 0.175 | 25 | 39 | 15.9 | 7.08 | 0.7503 |
| 7 | 0.146 | 37 | 38 | 15.8 | 7.07 | 0.7903 |

It can be seen from Table 6 above and FIG. 39 that all of the cakes rose, although there was some slight height variation. Cakes 6 and 7 had a relatively high rise after baking but shrank back on cooling. It was noted that cakes 4, 6 and 7 were slightly darker than the remainder and this correlates with a higher pH.

All of the cakes were crumbly on the date of manufacture but firmed-up after 24 hours.

There was no significant increase in water activity with reduced sodium content, and this indicates microbial stability for the cakes produced with the lower sodium content.

The cakes were judged by a tasting panel which was asked to assess each cake for (i) lightness of appearance, (ii) lightness of texture, and (iii) sweetness of taste.

The cakes with the most preferred appearance were 1 and 4; the least preferred were 3 and 6. The cakes with the most preferred texture were 1 and 2; the least preferred were 5 and 7. The sweetest cakes were 4 and 5, the least sweet were 1 and 2, although the scores for sweetness showed no real spread and the differences are likely to be due to personal preference.

The taste panel results demonstrate that, even though the sodium levels within the cakes have been reduced by almost 40% when compared with the control, there was no taste impact noted in the taste trials. The reduction in sodium did not correlate to the taste as perceived by the panel nor to any of the physical characteristics.

The height of the cakes in which added salt was replaced by SB20 (Recipe Nos. 4, 6 and 7) gave a reduced sodium level, a better rise and showed no impact on taste.

Example 25

This Example provides a further comparison between chocolate cakes produced in accordance with Recipes Nos. 1 and 4 in Example 24. Recipe No. 1 includes both conventional baking powder (the same as that used in Example 24) and salt. Recipe No. 4 uses the Eminate baking powder employed in Example 24 and also replaces the salt of Recipe No. 1 with 75% by weight of SB 20.

The Recipes used for this Example are shown in Tables 7 and 8 below:

TABLE 7

| Recipe No. 1 | |
| --- | --- |
| Ingredients | % |
| Sugar | 31.80% |
| Margarine | 23.10% |
| Wheat flour T55 | 17.25% |
| HOT WATER | 10.00% |
| Water | 8.00% |
| Cocoa powder | 5.00% |
| Pasteurized egg yolk | 1.80% |
| *Vanilla* flavor | 1.00% |
| Pasteurized egg albumen | 0.85% |
| Baking powder | 0.80% |
| Salt | 0.20% |
| Potassium sorbate | 0.20% |
| Total | 100.00% |

TABLE 8

| Recipe No. 4 | |
| --- | --- |
| Ingredients | % |
| Sugar | 31.80% |
| Margarine | 23.10% |
| Wheat flour T55 | 17.45% |
| HOT WATER | 10.00% |
| Water | 8.00% |
| Cocoa powder | 5.05% |
| Pasteurized egg yolk | 1.80% |
| Vanilla flavor | 1.00% |
| Pasteurized egg albumen | 0.85% |
| Baking powder | 0.60% |
| SB20 | 0.15% |
| Potassium sorbate | 0.20% |
| Total | 100.00% |

The chocolate cakes were prepared in accordance with the procedure described in Example 24 save that baking was effected for 20 minutes at 190° C.

The baked chocolate cakes were tested for pH, moisture content and water activity. The results are shown in Table 9.

TABLE 9

| | Recipe No. 1 | Recipe No. 4 |
| --- | --- | --- |
| pH | 6.62 (23.7° C.) | 6.97 (24.2° C.) |
| Moisture | 21.20% | 19.53% |
| Water Activity | 0.835 | 0.771 |

It was noted that the chocolate cake produced in accordance with Recipe No. 4 was slightly darker than that produced from Recipe No. 1. This could be due to the fact that the pH of the cake produced with Recipe No. 4 is nearer to neutral than that for the cake produced in accordance with Recipe No. 1.

The texture of the cake produced in accordance with Recipe No. 1 was noted to be firmer and denser than that produced from Recipe No. 4, which seemed to be softer and more crumbly. To provide more quantitative data, the "firmness" of 25 mm thick slices of the cake was measured with a texturometer using a plexiglass _P25L probe and a 5 kg load cell. The "firmness" was determined as the resistance of the cake vs the force applied for a penetration depth of 6 mm (see also American Institute of Baking Standard Procedure for Cake Firmness) The "firmness" of the cake produced from Recipe No. 1 was found to be about 460 grams whereas that produced from Recipe No. 4 was about 360 grams.

Panelists (n=24) were asked to evaluate "stickiness", "chocolate taste", "sweetness" and preference of the chocolate cakes produced from Recipes Nos. 1 and 4.

Each test consisted of paired comparison test of the abovementioned parameters: "which sample is MOST . . . ?".

A significant difference in "saltiness" was found, the chocolate cake produced from Recipe No. 1 being found to be more salty than that produced from Recipe No. 4 (p-value=0.0015).

No significant difference in "sweetness", "chocolate taste" or "stickiness" was found, but there was a strong tendency for the chocolate cake produced from Recipe No. 1 to be noted as "stickier" than that produced from Recipe No. 4.

Remarks about the samples showed that the chocolate cake produced from Recipe No. 1 was saltier and had less colour than that produced from Recipe No. 4. Remarks also showed that the cake prepared from Recipe No. 4 was more crumbly and darker than that produced from Recipe No. 1.

Example 26

This Example demonstrates production of muffins using baking powders containing the sodium bicarbonate product in accordance with the invention and, for the purposes of comparison, muffins produced using a conventional, commercially available baking powder.

The conventional baking powder was the same as the one used in Example 24 and comprised about 28% by weight sodium bicarbonate, about 39% by weight SAPP, and about 33% by weight low moisture flour.

The ingredients used for producing muffins incorporating the conventional baking powder are shown in Table 10.

TABLE 10

| Ingredients | % |
| --- | --- |
| Wheat flour | 28.00% |
| Native corn starch | 3.50% |
| Water | 17.00% |
| Sunflower oil | 14.00% |
| Caster fine sugar | 24.50% |
| Semi skimmed milk | 6.10% |
| Pasteurized egg yolk | 3.35% |
| Pasteurized white egg | 1.90% |
| Baking powder | 1.00% |
| Vanilla flavour | 0.35% |
| Emulsifiers (DATEM) | 0.15% |
| Emulsifiers (SSL) | 0.15% |
| Total | 100.00% |

Two different baking powder formulations incorporating the sodium bicarbonate product of the invention were used for producing muffins based on a slight variation of the above recipe. For both of these baking powder formulations, the sodium bicarbonate product was that designated in Example 24 as SB20 (in which the organic material was Gum Arabic and the particle size was approximately 15-20 μm). The compositions of these two baking powders differed in the leavening agent, one incorporating sodium acid pyrophosphate (SAPP) and the other incorporating monohydrated calcium pyrophosphate (MCP). The two baking powder formulations were as follows:

a) 30% by weight SB20, 45% by weight SAPP, and 25% by weight low moisture flour.
b) 30% by weight SB20, 45% by weight MCP, and 25% by weight low moisture flour.

MCP was chosen as a leavening agent for the purposes of this Example since it is a fast acting leavening agent that is often used to produce muffins.

Muffins were produced using the baking powder formulations (a) and (b) in the recipe of Table 4 instead of the conventional baking powder and using only 75% of the amount thereof (thus giving a reduction in the amount of baking powder of 25%).

Muffins produced using MCP as the leavening agent (i.e. baking powder (b)) will contain less sodium than those produced using SAPP since there is no sodium in the MCP.

All muffins were produced using the following procedure.
1. Dissolve egg powders and emulsifiers in water in Kenwood mixer (speed 1, 2 minutes).
2. Add sunflower oil and flavor to eggs in Kenwood mixer (speed 1, 2 minutes).
3. Sift and mix the dried ingredients: wheat flour, sugar, starch, skimmed milk powder and baking powder.
4. Add this liquid preparation part to dried blend.
5. Mix to obtain an homogenous dough: speed 1, 1 minute and then speed 3, 3 minutes.
6. Fill each mould with 350 g of batter.
7. Cook 20 min. at 180° C. in a preheated deck oven.

The muffins produced were, in all cases, more similar to cupcakes rather than muffins.

Figure 40:
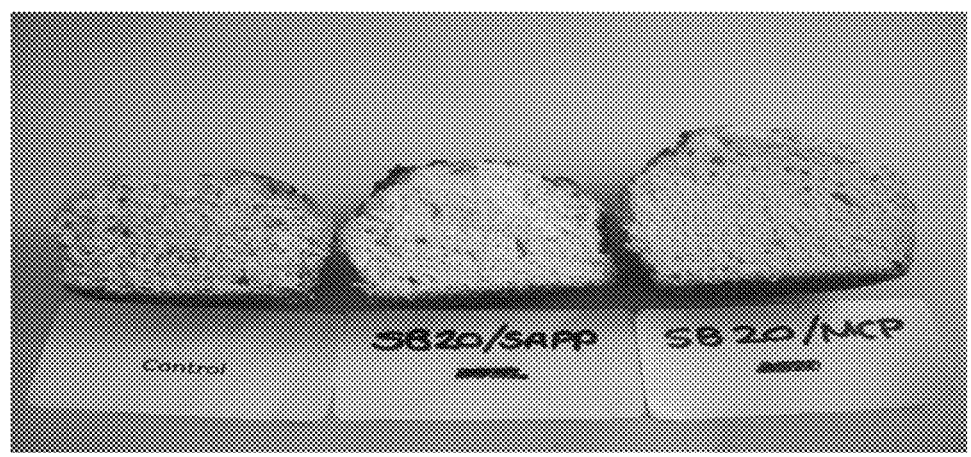

The muffins were photographs both "whole" and "cut through", the results being shown in FIGS. 40 (a) and (b) respectively. It can be seen from FIGS. 40 (a) and (b) that there were differences between the muffins produced with the various baking powders. The muffins produced with the baking powders ((a) and (b)) containing the sodium bicarbonate product (SB20) in accordance with the invention had a higher rise than that produced with the commercially available baking powder. We believe this is due to higher gas evolution. The highest rise was provided by the muffin prepared with baking powder (b) (i.e. incorporating SB20 and MCP as leavening agent). The structure inside all of the muffins was similar, but there were smaller bubbles in the muffins produced with the baking powders incorporating SB20, which may be due to the particle size and distribution throughout the dough.

There is also a colour difference between the three different types of muffin, the SB20/SAPP mix giving a brightest internal colour.

The muffins were tested for pH, water activity and height. The results are shown in Table 11, which also includes the sodium content of the muffins and the % reduction for muffins produced with incorporating the SB20.

TABLE 11

| Muffin | Sodium content (%) | Sodium reduction (%) | pH | Water activity | Height (mm) |
|---|---|---|---|---|---|
| Control | 0.22 | | 7.06 | 0.72 | 52 |
| SB20 with SAPP | 0.17 | 33 | 7.04 | 0.7 | 52 |
| SB20 with MCP | 0.14 | 46 | 7.3 | 0.72 | 54 |

All muffins were tested for taste by an informal panel. All muffins were judged to have a similar taste but when the panelists were asked to choose a favorite the muffin prepared with the baking powder of SB20 and MCP was selected, but it was noted that the other muffins both had an acceptable taste.

Example 27

This Example provides a further comparison of muffins produced using (a) conventional baking powder, and (b) a sodium bicarbonate product in accordance with the invention in conjunction with MCP as a source of a leavening acid. The conventional baking powder was the same as that used in Example 24. The sodium bicarbonate product in accordance with the invention was SB20 as described in Example 24.

Table 11 below shows the recipe for the muffin produced with conventional baking powder whereas Table 12 shows the recipe for the muffin prepared with SB20. It should be noted that neither recipe contain salt.

To prepare the muffins, all dried ingredients were initially sieved. The egg powder was then dissolved in the water and the emulsifiers, oil and flavour added. The remaining dried ingredients were added and mixing effected to produce a dough which was then introduced into muffin moulds (40 grams). The muffins were then baked in a preheated oven.

The muffins obtained were analysed for pH, moisture content and water activity. The results are shown in Table 12 below.

TABLE 12

| | Comparative Recipe | Recipe with SB20 |
|---|---|---|
| pH | 6.76 | 6.60 |
| Moisture | 12.3% | 12.9% |
| Water Activity | 0.720 | 0.727 |

The muffin produced with SB20 was noted to be of a darker colour, possibly due to its slightly lower pH (than was the case for the muffin produced from the comparative recipe).

Both types of muffin were tested by an informal panel. All muffins were noted to have a relatively dense structure but soft texture. Both types of muffins were noted to be sweet and have a vanilla flavour.

One difference noted was that a few tunnels were observed in the crumb of the muffins produced with SB20.

The invention claimed is:

1. A sodium bicarbonate product which comprises particles containing sodium bicarbonate and an organic material that is a solid at ambient temperature, the particles of said product having a structure comprising individual crystallites of sodium bicarbonate attached together in the particle wherein more than 95% by volume of the particles have a size less than 200 μm and wherein at least a fraction of the particles of the product are hollow and are formed of an outer shell of said crystallites.

2. A product as claimed in claim 1 wherein more than 95% by volume of the particles have a size less than 125 μm.

3. A product as claimed in claim 1 having a mean particle size in the range of 50 μm to 100 μm.

4. A product as claimed in claim 1 wherein more than 95% by volume of the particles have a size less than 75 μm.

5. A product as claimed in claim 4 wherein more than 95% by volume of the particles have a size less than 50 μm.

6. A product as claimed in claim 5 wherein more than 75% by volume of the particles have a size less than 30 μm.

7. A product as claimed in claim 1 wherein at least 30% of the particles are hollow.

8. A product as claimed in claim 1 wherein at least 60% of the particles are hollow.

9. A product as claimed in claim 1 wherein at least 80% of the particles are hollow.

10. A product as claimed in claim 1 wherein the hollow particles are spheroidal and the shell comprises rod-like crystallites.

11. A product as claimed in claim 1 wherein the organic material comprises at least one polymeric material.

12. A product as claimed in claim 11 wherein the polymeric material is at least one of a carbohydrate, protein or synthetic organic polymer.

13. A product as claimed in claim 12 wherein the carbohydrate is an oligosaccharide or a polysaccharide.

14. A product as claimed in claim 12 wherein the polymeric material comprises at least one carbohydrate selected from maltodextrin, Gum Arabic, starch, Carrageenan, Hydroxypropyl cellulose, agar agar, locust bean gum, gellan gum, low acyl gellan gum, xanthan gum, pectin or gluco fibre.

15. A product as claimed in claim 14 wherein the carbohydrate is Gum Arabic.

16. A product as claimed in claim 14 wherein the carbohydrate is maltodextrin.

17. A product as claimed in claim 12 wherein the polymer comprises a synthetic organic polymer which is poly(ethylene glycol).

18. A product as claimed in claim 1 wherein the organic material is suitable for alimentary use.

19. A product as claimed in claim 1 wherein the particles consist essentially of said sodium bicarbonate and said organic material.

20. A product as claimed in claim 1 wherein the particles consist of said sodium bicarbonate and said organic material.

21. A baking powder comprising a sodium bicarbonate product as claimed in claim 1 and a source of a leavening acid.

22. A baking powder as claimed in claim 21 additionally comprising a storage enhancing agent.

23. A baking powder as claimed in claim 22 which comprises 28% to 30% by weight of the sodium bicarbonate product, 43% to 47% by weight of the source of a leavening acid, and 31% to 35% by weight of the storage enhancing agent.

24. A baking powder as claimed in claim 22 wherein the storage enhancing agent is a low moisture flour.

25. A baking powder as claimed in claim 21 wherein the source of the leavening acid is sodium acid pyrophosphate, monohydrated calcium pyrophosphate, anhydrous monocalcium phosphate or sodium aluminium phosphate.

26. A method for providing antimicrobial properties to a composition, the method comprising including an antimicrobially-effective amount of a product as claimed in claim 1 in the composition.

27. A method for leavening food, the method comprising including a product as claimed in claim 18 as a leavening agent in a food composition.

28. A method for producing blown plastic or rubber material, the method comprising including a product as claimed in claim 1 as a blowing agent in a plastic or rubber composition.

29. A method of producing a sodium bicarbonate product comprising the steps of:
   (i) preparing an aqueous admixture which comprises sodium bicarbonate and a water soluble organic material that is a solid at ambient temperature, the sodium bicarbonate and the organic material both being at least partially dissolved in the aqueous phase, and
   (ii) atomising said admixture and evaporating water to produce a sodium bicarbonate product in which particles of said product have a structure comprising individual crystallites of sodium bicarbonate attached together in the particle wherein more than 95% by volume of the particles have a size less than 200 μm and wherein particles of the product are hollow and are formed of an outer shell of said crystallites.

30. A method as claimed in claim 29 wherein the ratio of the amount of sodium bicarbonate to the amount of organic material in the aqueous admixture is in the range 5:1 to 35:1.

31. A method as claimed in claim 29 wherein the aqueous admixture contains a suspension of sodium bicarbonate.

32. A method as claimed in claim 29 wherein the aqueous admixture comprises 100 to 1000 grams of sodium bicarbonate per liter of water.

33. A method as claimed in claim 29 wherein the atomisation and evaporation steps are effected by spray drying.

34. A method as claimed in claim 29 wherein the sodium bicarbonate used for preparing the aqueous admixture is at least 95% by weight pure (excluding any water of crystallisation).

35. A method as claimed in claim 29 wherein the organic material comprises at least one polymeric material.

36. A method as claimed in claim 35 wherein the polymeric material is at least one of a carbohydrate, protein or synthetic organic polymer.

37. A method as claimed in claim 36 wherein the carbohydrate is an oligosaccharide or a polysaccharide.

38. A method as claimed in claim 36 wherein the polymeric material comprises at least one carbohydrate selected from maltodextrin, Gum Arabic, starch, Carrageenan, Hydroxypropyl cellulose, agar agar, locust bean gum, gellan gum, low acyl gellan gum, xanthan gum, pectin or gluco fibre.

39. A method as claimed in claim 38 wherein the carbohydrate is Gum Arabic.

40. A method as claimed in claim 38 wherein the carbohydrate is maltodextrin.

41. A method as claimed in claim 36 wherein the polymer comprises a synthetic organic polymer which is poly(ethylene glycol).

42. A method as claimed in claim 29 wherein the loose bulk density of the sodium bicarbonate product is 80 to 98% of the loose bulk density of the sodium bicarbonate from which the product was prepared.

43. A method of producing a sodium bicarbonate product comprising the steps of:
(i) preparing a first aqueous solution of a water soluble organic material that is a solid at ambient temperature by a dissolution process effected such that the temperature of the aqueous solution does not exceed 30° C., said aqueous solution containing 0.1 to 40 g of the organic material per liter of water;
(ii) heating the first aqueous solution prepared in step (i) to a temperature in the range 50° to 65° C.;
(iii) preparing a second aqueous solution by dissolving sodium bicarbonate which is at least 95% by weight pure (excluding any water of crystallization) into the first aqueous solution from step (ii) in an amount of at least 100 g of sodium bicarbonate per liter of water whilst maintaining the aqueous phase at a temperature of 50° to 65° C.; and
(iv) atomising the second aqueous solution and evaporating water from the atomised droplets at a temperature of 50° to 70° C. to produce particles comprising bicarbonate and the organic material, wherein the particles of said product have a structure comprised of individual crystallites of sodium bicarbonate attached together in the particle wherein more than 95% by volume of the particles have a size less than 200 μm and wherein particles of the product are hollow and are formed of an outer shell of said crystallites.

44. A method of producing a cooked food product comprising preparing a mix from which the product is to be cooked, said mix incorporating a sodium bicarbonate product as claimed in claim 18, and cooking the mix to produce the foodstuff.

45. A method as claimed in claim 44 wherein the mix additionally incorporates a source of a leavening acid.

46. A method as claimed in claim 44 wherein the cooking comprises baking, roasting, grilling, frying or griddling.

47. A method as claimed in claim 44 wherein the cooked food product is a baked food product, the mix is a batter or a dough, and the cooking comprises baking the product.

48. A method as claimed in claim 47 wherein the baked food product is a cake or a muffin.

* * * * *